(12) United States Patent
Simon et al.

(10) Patent No.: US 8,481,723 B2
(45) Date of Patent: Jul. 9, 2013

(54) 3-(3,4-DIHYDRO-2H-BENZO[1,4]OXAZIN-6-YL)-1H-PYRIMIDIN-2,4-DIONE COMPOUNDS AS HERBICIDES

(75) Inventors: Anja Simon, Weinheim (DE); Liliana Parra Rapado, Offenburg (DE); Richard Roger Evans, Limburgerhof (DE); Matthias Witschel, Bad Duerkheim (DE); Trevor William Newton, Neustadt (DE); Thomas Seitz, Viernheim (DE); Helmut Walter, Obrigheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/509,138

(22) PCT Filed: Nov. 4, 2010

(86) PCT No.: PCT/EP2010/066778
§ 371 (c)(1),
(2), (4) Date: May 10, 2012

(87) PCT Pub. No.: WO2011/057935
PCT Pub. Date: May 19, 2011

(65) Prior Publication Data
US 2012/0231952 A1 Sep. 13, 2012

(30) Foreign Application Priority Data
Nov. 13, 2009 (EP) .................... 09175896

(51) Int. Cl.
*C07D 413/04* (2006.01)
*A01N 43/84* (2006.01)

(52) U.S. Cl.
USPC ................... 544/105; 514/230.5

(58) Field of Classification Search
USPC ............................. 544/105
See application file for complete search history.

(56) References Cited

U.S. PATENT DOCUMENTS

| 6,323,154 B1 | 11/2001 | Klintz et al. |
| 2004/0186021 A1 | 9/2004 | Schallner et al. |

FOREIGN PATENT DOCUMENTS

| CA | 2 033 346 | 12/1990 |
| DE | 195 08 590 | 9/1996 |
| WO | WO 90/15057 | 12/1990 |
| WO | WO 03/006461 | 1/2003 |
| WO | WO 2010/145992 | 12/2010 |
| WO | WO 2011/051393 | 5/2011 |

OTHER PUBLICATIONS

International Search Report completed Jan. 24, 2011, in International Application No. PCT/EP2010/066778, filed Nov. 4, 2010.
European Search Report completed Apr. 12, 2010, in a corresponding European Application.
International Preliminary Report on Patentability dated May 15, 2012, from corresponding International Application No. PCT/EP2010/066778, filed Nov. 4, 2010.

*Primary Examiner* — Kahsay T Habte
(74) *Attorney, Agent, or Firm* — Brinks Hofer Gilson & Lione

(57) ABSTRACT

The present invention relates to uracils of formula I

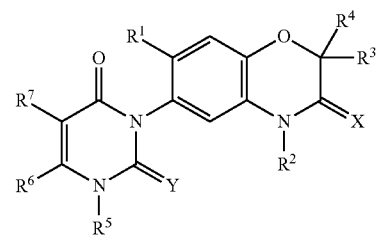

wherein the variables are defined according to the description, processes and intermediates for preparing the uracils of the formula I, compositions comprising them and their use as herbicides, i.e. for controlling harmful plants, and also a method for controlling unwanted vegetation which comprises allowing a herbicidal effective amount of at least one uracil of the formula I to act on plants, their seed and/or their habitat.

18 Claims, No Drawings

3-(3,4-DIHYDRO-2H-BENZO[1,4]OXAZIN-6-YL)-1H-PYRIMIDIN-2,4-DIONE COMPOUNDS AS HERBICIDES

This application is a National Stage application of International Application No. PCT/EP2010/066778, filed Nov. 4, 2010, the entire contents of which is hereby incorporated herein by reference. This application also claims priority under 35 U.S.C. §119 to European Patent Application No. 09175896.1 filed Nov. 13, 2009, the entire contents of which is hereby incorporated herein by reference.

The present invention relates to uracils of the general formula I defined below and to their use as herbicides. Moreover, the invention relates to compositions for crop protection and to a method for controlling unwanted vegetation.

WO 90/15057 for example describes inter alia structurally similar compounds for which herbicidal action is stated, which differ from the uracils I according to the present invention in that the benzo[1,4]oxazine ring is preferably unsubstituted in the 2-position or carries an alkyl group, whereas the uracils of formula I according to the present invention are substituted in said position by at least one halogen atom.

However, the herbicidal properties of these known compounds with regard to the harmful plants are not always entirely satisfactory.

It is therefore an object of the present invention to provide uracils having improved herbicidal action. To be provided are in particular uracils which have high herbicidal activity, in particular even at low application rates, and which are sufficiently compatible with crop plants for commercial utilization.

These and further objects are achieved by the uracils of the formula I, defined below, and by their agriculturally suitable salts.

Accordingly, the present invention provides uracils of formula I

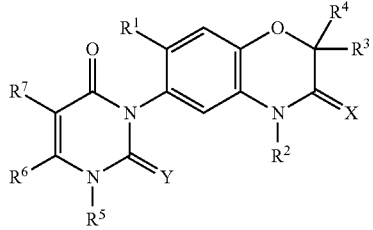

wherein
$R^1$ is hydrogen or halogen;
$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^3$ is hydrogen or halogen;
$R^4$ is halogen;
$R^5$ is hydrogen, $NH_2$, $C_1$-$C_6$-alkyl or $C_3$-$C_6$-alkynyl;
$R^6$ is hydrogen, $C_1$-$C_6$-alkyl or $C_1$-$C_6$-haloalkyl;
$R^7$ is hydrogen or $C_1$-$C_6$-alkyl;
X is O or S; and
Y is O or S;
including their agriculturally acceptable salts.

The present invention also provides herbicidally active compositions comprising at least one uracil of formula I and at least one further compound selected from herbicidal active compounds B and safeners C.

The present invention also provides the use of uracils of the general formula I as herbicides, i.e. for controlling harmful plants.

The present invention also provides mixtures comprising at least one uracil of the formula I and auxiliaries customary for formulating crop protection agents.

The present invention furthermore provides a method for controlling unwanted vegetation where a herbicidal effective amount of at least one uracil of the formula I is allowed to act on plants, their seeds and/or their habitat. Application can be done before, during and/or after the emergence of the undesirable plants.

Moreover, the invention relates to processes and intermediates for preparing uracils of the formula I.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope, of the invention.

As used herein, the terms "controlling" and "combating" are synonyms.

As used herein, the terms "undesirable vegetation" and "harmful plants" are synonyms.

If the uracils of formula I as described herein are capable of forming geometrical isomers, for example E/Z isomers, it is possible to use both, the pure isomers and mixtures thereof, in the compositions according to the invention.

If the uracils of formula I as described herein have one or more centers of chirality and, as a consequence, are present as enantiomers or diastereomers, it is possible to use both the pure enantiomers and diastereomers and their mixtures in the compositions according to the invention.

If the uracils of formula I as described herein have functional groups, which can be ionized, they can also be used in the form of their agriculturally acceptable salts or mixtures thereof.

In general, the salts of those cations are suitable whose cations have no adverse effect on the action of the active compounds ("agricultural acceptable"). Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

Anions of useful acid addition salts are primarily chloride, bromide, fluoride, iodide, hydrogen sulfate, methyl sulfate, sulfate, dihydrogen phosphate, hydrogen phosphate, nitrate, bicarbonate, carbonate, hexafluorosilicate, hexafluorophosphate, benzoate and the anions of $C_1$-$C_4$-alkanoic acids, preferably formate, acetate, propionate and butyrate.

The organic moieties mentioned in the definition of the variables mentioned herein, especially with regard to $R^1$ to $R^7$, are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl and also the $C_1$-$C_4$-alkyl moieties of $C_3$-$C_6$-cycloalkyl-$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and trisdecafluorohexyl;

$C_3$-$C_6$-cycloalkyl and also the cycloalkyl moieties of $C_3$-$C_6$-cycloalkyl-$C_1$-$C_6$-alkyl, $C_3$-$C_6$-cycloalkyxy: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and the alkenyl moieties of $C_2$-$C_6$-alkenyloxy, $C_2$-$C_6$-haloalkenyloxy: $C_3$-$C_6$-alkenyl as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl and also the $C_3$-$C_6$-alkynyl, moieties of $C_3$-$C_6$-alkynyloxy: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl and also the $C_3$-$C_6$-haloalkynyl moieties of $C_3$-$C_6$-haloalkynyloxy: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of $C_1$-$C_4$-alkoxy-$C_2$-$C_4$-alkoxy, $C_1$-$C_4$-alkylthio-$C_2$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-haloalkoxy, $C_1$-$C_6$-cyanoalkoxy: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3- dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-alkylthio and also the $C_1$-$C_4$-alkylthio moieties of $C_1$-$C_4$-alkylthio-$C_2$-$C_4$-alkoxy: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

aryl and also the aryl moiety of aryloxy: a mono- to trinuclear aromatic carbocycle having 6 to 14 ring members, such as for example, phenyl, maphthyl, anthravˊ cenyl and phenanthrenyl.

The preferred embodiments of the invention mentioned herein below have to be understood as being preferred either independently from each other or in combination with one another.

According to a preferred embodiment of the invention preference is also given to those uracils of formula I, wherein the variables, either independently of one another or in combination with one another, have the following meanings:

$R^1$ is hydrogen;
  is also preferably halogen,
  particularly preferred F or Cl,
  especially preferred F;
$R^2$ is $C_3$-$C_6$-alkynyl or $C_3$-$C_6$-haloalkynyl,
  preferably $C_3$-alkynyl or $C_3$-haloalkynyl,
  particularly preferred $CH_2C{\equiv}CH$, $CH_2C{\equiv}CCl$ or $CH_2C{\equiv}CBr$;
  is also preferably $C_3$-$C_6$-alkynyl or $C_3$-$C_6$-cycloalkyl-$C_1$-$C_6$-alkyl,
  particularly preferred propargyl or cyclopropylmethyl;
  is also preferably $C_3$-$C_6$-alkynyl, preferably $C_3$-alkynyl;
  particularly preferred $CH_2C{\equiv}CH$;
  is also preferably $C_3$-$C_6$-haloalkynyl, preferably $C_3$-haloalkynyl,
  particularly preferred $CH_2C{\equiv}CCl$ or $CH_2C{\equiv}CBr$;
$R^3$ is hydrogen;
  is also preferably halogen, particularly preferred F;
  is also preferably hydrogen or F;
$R^4$ is F;
$R^5$ is hydrogen, $NH_2$ or $C_1$-$C_6$-alkyl,
  preferably $NH_2$ or $C_1$-$C_4$-alkyl,
  particularly preferred $NH_2$ or $CH_3$;
  is also preferably $C_1$-$C_6$-alkyl,
  preferably $C_1$-$C_4$-alkyl, particularly preferred $CH_3$;
$R^6$ is $C_1$-$C_6$-alkyl or $C_1$-$C_6$-haloalkyl,
  preferably $C_1$-$C_4$-alkyl or $C_1$-$C_4$-haloalkyl,
  more preferred $C_1$-$C_4$-haloalkyl;
  particularly preferred $C_1$-$C_2$-haloalkyl; especially preferred $CF_3$
$R^7$ is hydrogen;
  is also preferably $C_1$-$C_6$-alkyl,
  preferably $C_1$-$C_4$-alkyl,
  particularly preferred $CH_3$;

X is O,
  is also preferably S
Y is O,
  is also preferably S.

Particular preference is given to uracils of formula I, wherein $R^4$ is F, $R^5$ is $CH_3$, $R^6$ is $CF_3$, $R^7$ is hydrogen, X is O and Y is O, and which herein below are also referred to as

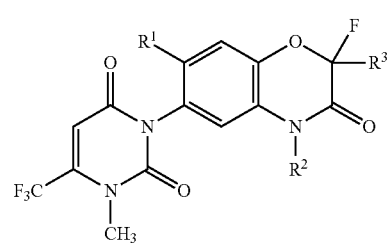

Ia wherein the variables $R^1$, $R^2$ and $R^3$ have the meanings, in particular the preferred meanings, as defined above.

Special preference is given to uracils of the formulae Ia1 to Ia60 of table A, where the definitions of the variables $R^1$, $R^2$ and $R^3$ are of particular importance for the compounds according to the invention not only in combination with one another but in each case also on their own:

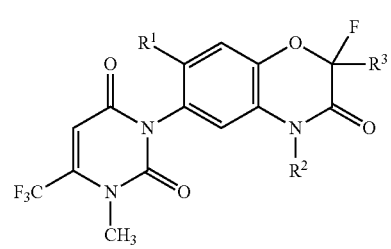

Ia

TABLE A

| no. | $R^1$ | $R^2$ | $R^3$ |
|---|---|---|---|
| Ia1 | H | H | H |
| Ia2 | H | $CH_3$ | H |
| Ia3 | H | $C_2H_5$ | H |
| Ia4 | H | $CH_2$—$C_2H_5$ | H |
| Ia5 | H | $CH(CH_3)_2$ | H |
| Ia6 | H | $CH_2$—$CH_2$—$(CH_3)_2$ | H |
| Ia7 | H | $CH_2$—$CH{=}CH_2$ | H |
| Ia8 | H | $CH_2C{\equiv}CH$ | H |
| Ia9 | H | $CH_2C{\equiv}C$—Cl | H |
| Ia10 | H | $CH_2C{\equiv}C$—Br | H |
| Ia11 | F | H | H |
| Ia12 | F | $CH_3$ | H |
| Ia13 | F | $C_2H_5$ | H |
| Ia14 | F | $CH_2$—$C_2H_5$ | H |
| Ia15 | F | $CH(CH_3)_2$ | H |
| Ia16 | F | $CH_2$—$CH_2$—$(CH_3)_2$ | H |
| Ia17 | F | $CH_2$—$CH{=}CH_2$ | H |
| Ia18 | F | $CH_2C{\equiv}CH$ | H |
| Ia19 | F | $CH_2C{\equiv}C$—Cl | H |
| Ia20 | F | $CH_2C{\equiv}C$—Br | H |
| Ia21 | Cl | H | H |
| Ia22 | Cl | $CH_3$ | H |
| Ia23 | Cl | $C_2H_5$ | H |
| Ia24 | Cl | $CH_2$—$C_2H_5$ | H |
| Ia25 | Cl | $CH(CH_3)_2$ | H |
| Ia26 | Cl | $CH_2$—$CH_2$—$(CH_3)_2$ | H |
| Ia27 | Cl | $CH_2$—$CH{=}CH_2$ | H |

TABLE A-continued

| no. | $R^1$ | $R^2$ | $R^3$ |
|---|---|---|---|
| Ia28 | Cl | $CH_2C\equiv CH$ | H |
| Ia29 | Cl | $CH_2C\equiv C-Cl$ | H |
| Ia30 | Cl | $CH_2C\equiv C-Br$ | H |
| Ia31 | H | H | F |
| Ia32 | H | $CH_3$ | F |
| Ia33 | H | $C_2H_5$ | F |
| Ia34 | H | $CH_2-C_2H_5$ | F |
| Ia35 | H | $CH(CH_3)_2$ | F |
| Ia36 | H | $CH_2-CH_2-(CH_3)_2$ | F |
| Ia37 | H | $CH_2-CH=CH_2$ | F |
| Ia38 | H | $CH_2C\equiv CH$ | F |
| Ia39 | H | $CH_2C\equiv C-Cl$ | F |
| Ia40 | H | $CH_2C\equiv C-Br$ | F |
| Ia41 | F | H | F |
| Ia42 | F | $CH_3$ | F |
| Ia43 | F | $C_2H_5$ | F |
| Ia44 | F | $CH_2-C_2H_5$ | F |
| Ia45 | F | $CH(CH_3)_2$ | F |
| Ia46 | F | $CH_2-CH_2-(CH_3)_2$ | F |
| Ia47 | F | $CH_2-CH=CH_2$ | F |
| Ia48 | F | $CH_2C\equiv CH$ | F |
| Ia49 | F | $CH_2C\equiv C-Cl$ | F |
| Ia50 | F | $CH_2C\equiv C-Br$ | F |
| Ia51 | Cl | H | F |
| Ia52 | Cl | $CH_3$ | F |
| Ia53 | Cl | $C_2H_5$ | F |
| Ia54 | Cl | $CH_2-C_2H_5$ | F |
| Ia55 | Cl | $CH(CH_3)_2$ | F |
| Ia56 | Cl | $CH_2-CH_2-(CH_3)_2$ | F |
| Ia57 | Cl | $CH_2-CH=CH_2$ | F |
| Ia58 | Cl | $CH_2C\equiv CH$ | F |
| Ia59 | Cl | $CH_2C\equiv C-Cl$ | F |
| Ia60 | Cl | $CH_2C\equiv C-Br$ | F |

Also preferred are the uracils of formula Ib, particularly preferred the uracils of formulae Ib1 to Ib60, which differ from the corresponding uracils of formulae Ia1 to Ia60 only in

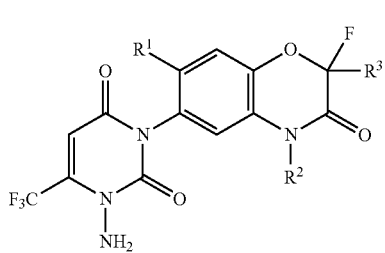

Ib

Also preferred are the uracils of formula Ic, particularly preferred the uracils of formulae Ic1 to Ic60, which differ from the corresponding uracils of formulae Ia1 to Ia60 only in that $R^5$ is hydrogen:

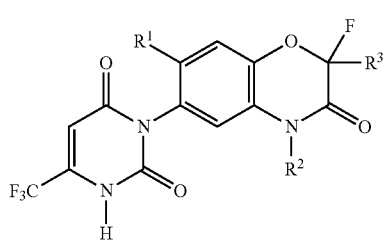

Ic

The uracils of formula I according to the invention can be prepared by standard processes of organic chemistry, for example by reaction of an iso(thio)cyanate of the formula II with an enamine of the formula III:

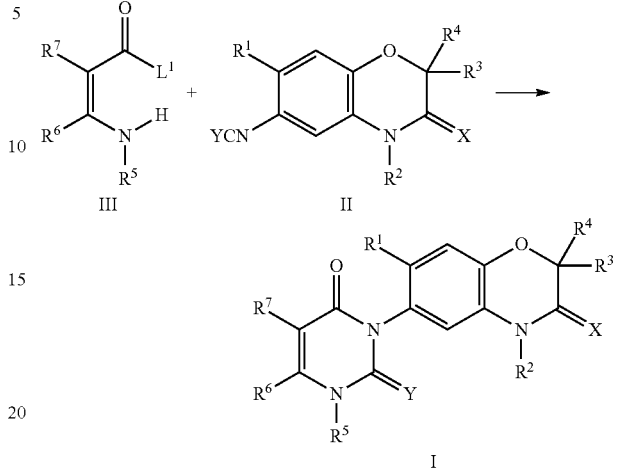

The variables $R^1$ to $R^7$, X and Y are each as defined above, preferably as defined with preference.

In a preferred embodiment of this reaction of an isocyanate of the formula II with an enamine of the formula III, $R^5$ is preferably hydrogen, $C_1$-$C_6$-alkyl or $C_3$-$C_6$-alkynyl; more preferably hydrogen or $C_1$-$C_6$-alkyl, most preferably hydrogen.

$L^1$ is a nucleophilically displaceable leaving group;
preferably $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2$-$C_4$-alkoxy, $C_2$-$C_6$-alkenyloxy, $C_2$-$C_6$-haloalkenyloxy, $C_3$-$C_6$-alkynyloxy, $C_3$-$C_6$-haloalkynyloxy, $C_3$-$C_6$-cycloalkyloxy, $C_1$-$C_6$-cyanoalkoxy or benzyloxy, which may itself be partly or fully halogenated on the phenyl ring and/or may be substituted by from one to three radicals from the group of cyano, nitro, $C_1$-$C_4$-alkyl, $C_1$-$C_4$-alkoxy and $C_1$-$C_4$-alkylthio;

more preferably $C_1$-$C_6$-alkoxy, $C_1$-$C_6$-haloalkoxy, $C_1$-$C_4$-alkoxy-$C_2$-$C_4$-alkoxy, $C_2$-$C_6$-alkenyloxy, $C_2$-$C_6$-haloalkenyloxy, $C_3$-$C_6$-alkynyloxy or $C_3$-$C_6$-haloalkynyloxy;

very preferably $C_1$-$C_6$-alkoxy, $C_1$-$C_4$-alkoxy-$C_2$-$C_4$-alkoxy, $C_2$-$C_6$-alkenyloxy or $C_3$-$C_6$-alkynyloxy;

particularly preferably $C_1$-$C_6$-alkoxy.

This reaction of the iso(thio)cyanates of the formula II with enamines of the formula III are usually carried out for example from −20° C. to 80° C. in an inert organic solvent in the presence of a base (e.g. WO 05/054208).

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, diethylene glycol dimethyl ether, anisole and tetrahydrofuran, nitriles such as acetonitrile and propionitrile, alcohols such as methanol, ethanol, n-propanol, isopropanol, n-butanol and tert-butanol, carboxylic esters such as butyl acetate, and also dimethyl sulfoxide, dimethylformamide, dimethylacetamide and N-methylpyrrolidone; more preferably dimethylformamide, dimethylacetamide and N-methylpyrrolidone.

It is also possible to use mixtures of the solvents mentioned.

Useful bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, calcium carbonate and cesium carbonate, and also alkali metal hydrogencarbonates such as sodium hydrogencarbonate, organometallic compounds, especially alkali metal alkyls such as methyllithium, butyllithium and phenyllithium, alkali metal and alkaline earth metal alkoxides such as lithium methoxide, sodium methoxide, sodium ethoxide, potassium ethoxide, potassium tert-butoxide, potassium tert-pentoxide and dimethoxymagnesium, and also organic bases, for example tertiary amines such as trimethylamine, triethylamine, diisopropylethylamine and N-methylpiperidine, pyridine, substituted pyridines such as collidine, lutidine and 4-dimethylaminopyridine, and also bicyclic amines. Particular preference is given to alkali metal and alkaline earth metal hydroxides, alkali metal and alkaline earth metal carbonates and also alkali metal and alkaline earth metal alkoxides.

The bases are generally used in excess, based on the isocyanate of the formula II, and they may also be used as the solvent. It may be advantageous to add the base offset over a period of time.

The reaction mixtures are worked up in a customary manner, for example by mixing with water, separation of the phases and if appropriate, chromatographic purification of the crude product. Some of the intermediates and end products are obtained in the form of viscous oils, which can be purified or freed from volatile components under reduced pressure and at moderately elevated temperature. If the intermediates and the end products are obtained as solid, purification can also be carried out by recrystallisation or digestion.

The iso(thio)cyanates of formula II in turn can be obtained from the corresponding amine compounds IV:

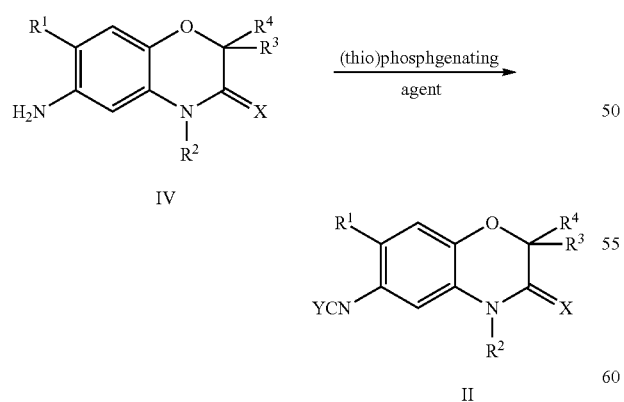

IV

II

Suitable (thio)phosgenating agents are phosgene, diphosgene or triphosgene and each of the respective thio derivatives, diphosgene being preferred.

The reaction of the amine IV is usually carried out at from −20° C. to the boiling point of the reaction mixture, preferably at from 10° C. to 200° C., particularly preferably at from 20° C. to 150° C., in an inert organic solvent and, if appropriate, in the presence of a base (e.g. WO 04/39768).

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to aromatic hydrocarbons such as toluene, o-, m- and p-xylene. It is also possible to use mixtures of the solvents mentioned.

Suitable bases are, in general inorganic compounds such as alkali metal and alkaline earth metal carbonates such as lithium carbonate, potassium carbonate and calcium carbonate, as well as alkali metal bicarbonates such as sodium bicarbonate, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as triethylamine. The bases are generally employed in catalytic amounts, however they can also be employed in equimolar amounts, in excess or, if appropriate, be used as solvent.

Work up can be carried out in a known manner.

The enamines of the formula III also required for the preparation of the uracils of formula I are disclosed in the literature (for example A. Lutz, A. and S. Trotto, J. of Heterocyclic Chem. 1972, 9, 3, 513-522) and can be prepared in accordance.

The uracils of formula I according to the invention can also be prepared by reacting a (thio)carbamate of the formula V with an enamine of the formula III:

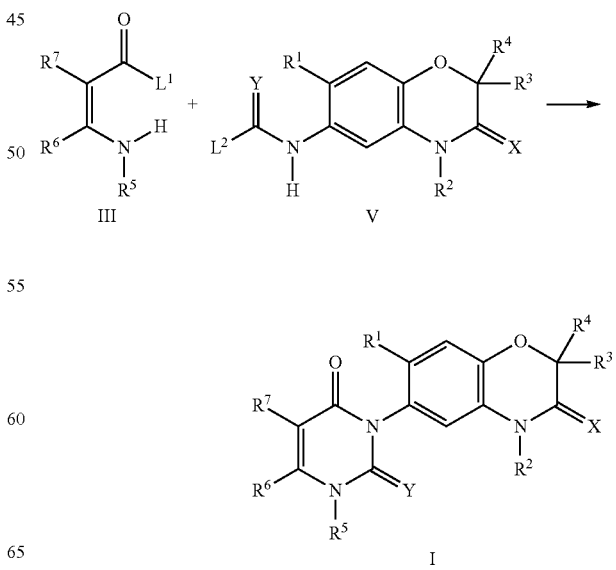

I

The variables $R^1$ to $R^7$, X, Y and $L^1$ are each as defined above, preferably as defined with preference.

$L^2$ is a nucleophilically displaceable leaving group,
preferably $C_1$-$C_6$-alkoxy, $C_1$-$C_6$-alkylthio or aryloxy, wherein the aryl moiety may itself be partly or fully halogenated and/or may be substituted by from one to three radicals from the group of cyano, nitro, $C_1$-$C_4$-alkyl, $C_1$-$C_4$-alkoxy and $C_1$-$C_4$-alkylthio;
particularly preferably $C_1$-$C_6$-alkoxy, $C_1$-$C_6$-alkylthio or phenyloxy, wherein the phenyl moiety may itself be partly or fully halogenated and/or may be substituted by from one to three radicals from the group of cyano, nitro, $C_1$-$C_4$-alkyl, $C_1$-$C_4$-alkoxy and $C_1$-$C_4$-alkylthio;
more preferably $C_1$-$C_6$-alkoxy, $C_1$-$C_6$-alkylthio or phenyloxy;
most preferably $C_1$-$C_6$-alkoxy.

This reaction of the (thio)carbamates of the formula V with enamines of the formula III is effected typically at temperatures above room temperature, for example from 25° C. to 200° C., preferably from 90° C. to 190° C., more preferably from 100° C. to 140° C. in an inert organic solvent in the presence of a base (e.g. WO 99/31091).

Suitable solvents and bases are those mentioned above with regard to the reaction of the isocyanate of the formula II with an enamine of the formula III.

The (thio)carbamates of the formula V required for the preparation of the uracils of formula I may be prepared in analogy to known processes (for example Houben-Weyl, Methoden der organischen Chemie [Methods of organic chemistry], E5, 1985, p. 972-980, and also VIII, p. 655 and XI part 2, p. 10) by reacting an amine of the formula IV with a compound of the formula X

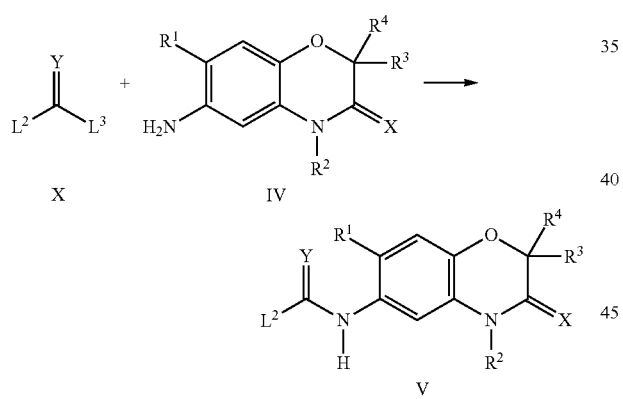

wherein $R^1$ to $R^4$, X, Y and $L^2$ are each as defined above and $L^3$ is a nucleophilically displaceable leaving group.

The (thio)carbamates of the formula V are novel compounds and, as shown above, suitable intermediates for the preparation of the uracils of formula I according to the present invention.

Therefore the present invention also relates to (thio)carbamates of the formula V

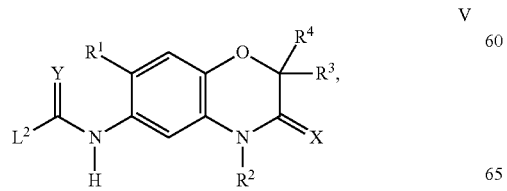

wherein $R^1$ is hydrogen or halogen;

$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$R^3$ is hydrogen or halogen;

$R^4$ is halogen;

X is O or S;

Y is O or S; and $L^2$ is a nucleophilically displaceable leaving group,
preferably $C_1$-$C_6$-alkoxy or $C_1$-$C_6$-alkylthio,
more preferably $C_1$-$C_6$-alkoxy.

With respect to the variables, the particularly preferred embodiments of the intermediate (thio)carbamates of the formula V correspond, either independently of one another or in combination with one another, to those of the variables of $R^1$, $R^2$, $R^3$, $R^4$, X and Y of the uracils of formula I.

The compounds of the formula X required for the preparation of the (thio)carbamates of the formula V are disclosed in the literature (for example Houben-Weyl, Methoden der organischen Chemie, E4, 1983, p. 6-17) and can be prepared accordingly or purchased commercially.

Those uracils of formula I, wherein $R^5$ is $NH_2$, $C_1$-$C_6$-alkyl or $C_3$-$C_6$-alkynyl, can also be prepared by amination or alkylation of those uracils of formula I, wherein $R^5$ is H:

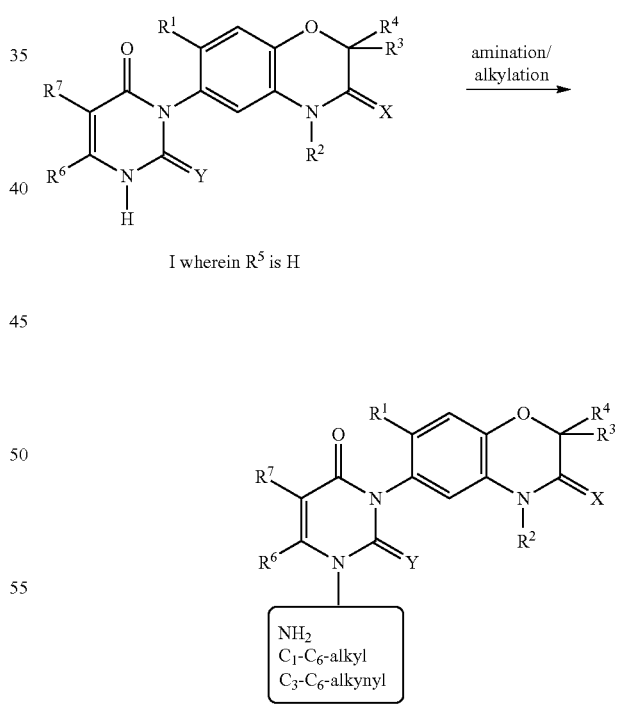

The amination or alkylation can be conducted in analogy to known processes (e.g. WO 05/054208; WO06/125746).

The amino compounds IV required for the preparation of the (thio)carbamates of the formula II can be obtained from the corresponding nitro compounds VI:

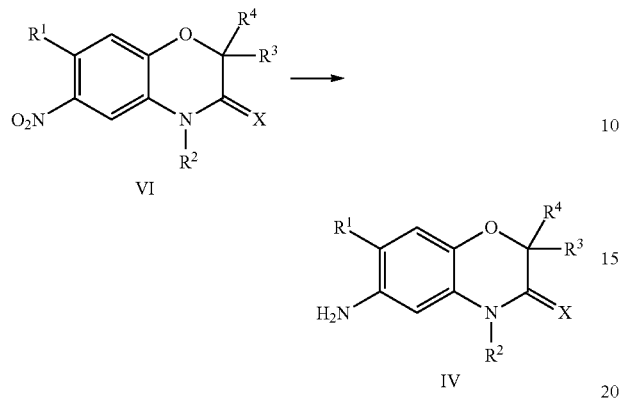

Preferred is the amino compound IVa (=amino compound IV wherein $R^4$ is fluorine and X is O):

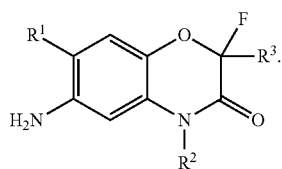

The reduction of the nitro compounds VI is usually carried out at from 20° C. to the boiling point of the reaction mixture, preferably at from 20° C. to 200° C., particularly preferably at from 20° C. to 100° C., in an inert organic solvent [Organikum, Heidelberg, 1993, pages 320-323].

Suitable reducing agents are nascent $H_2$; hydrogen in the presence of catalytic amounts of transition metals or transition metal compounds, in particular those of the $8^{th}$ transition group, preferably Ni, Pd, Pt, Ru or Rh, either as such, in supported form e.g. supported via activated carbon, Al, $ZrO_2$, $TiO_2$, $SiO_2$, carbonates and the like, or in compounds such as palladium oxide or platinum oxide; or metal hydrides, semimetal hydrides such as aluminium hydride and hydrides derived therefrom such as lithium aluminium hydride, diisobutylaluminiumhydride, borohydrides such as diborane or boranates derived therefrom such as sodium borohydride or lithium borohydride.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, alcohols such as methanol, ethanol, n-propanol, isopropanol, n-butanol and tert.-butanol, Particular preference is given to toluene and methanol. It is also possible to use mixtures of the solvents mentioned.

Work up can be carried out in a known manner.

The nitro compounds VI in turn can be obtained from the corresponding phenyl compounds VII:

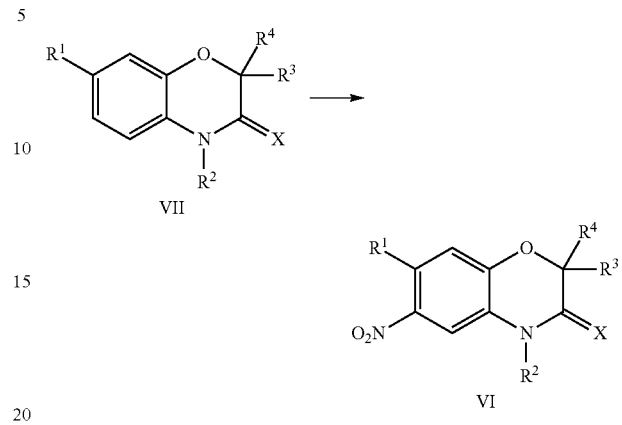

The nitration of the phenyl compound VII is usually carried out at from −20° C. to 100° C., particularly preferably at from 0° C. to 20° C. [Organikum, Heidelberg, 1993, pages 553-557].

Suitable nitrating agents are mixtures of $H_2SO_4{}_{conc}$ and $HNO_3{}_{conc}$, preferably in a range of 50:1 to 1:50, more preferably 20:1 to 1:20, especially preferred in a range of 10:1 to 1:10.

Work up can be carried out in a known manner.

Those nitro compounds VI, wherein $R^2$ is $C_3$-$C_6$-alkenyl, $C_3$-$C_6$-haloalkenyl, $C_3$-$C_6$-alkynyl or $C_3$-$C_6$-haloalkynyl, preferably $C_3$-$C_6$-alkynyl, can also be prepared by alkylation of nitro compounds VI, wherein $R^2$ is H:

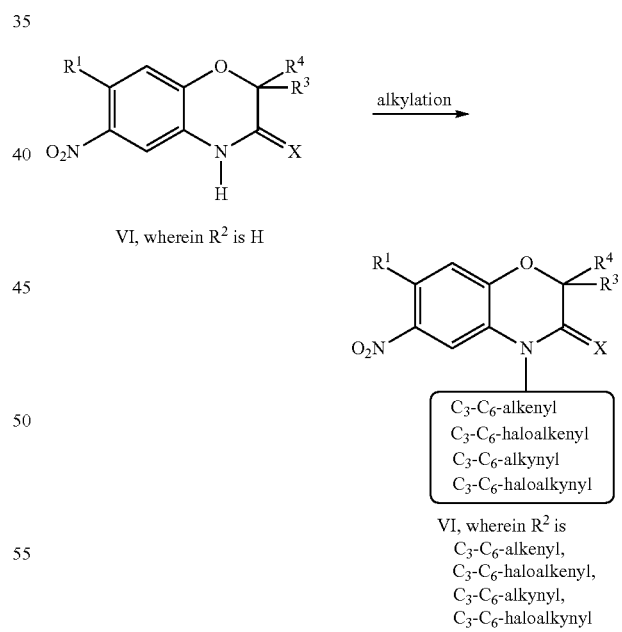

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to ethers such as diethyl ether, diisopropyl ether, tert.-butyl methyl ether, dioxane, anisole and tetrahydrofuran. It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as trimethylamine, triethylamine, diisopropylethylamine and alkali metal and alkaline earth metal alkoxides such as sodium methoxide, sodium ethoxide, potassium ethoxide, The bases are generally employed in catalytic amounts; however they can also be employed in equimolar amounts, in excess or, if appropriate, be used as solvent.

Work up can be carried out in a known manner.

The phenyl compounds VII in turn can be obtained from the corresponding acetamides VIII:

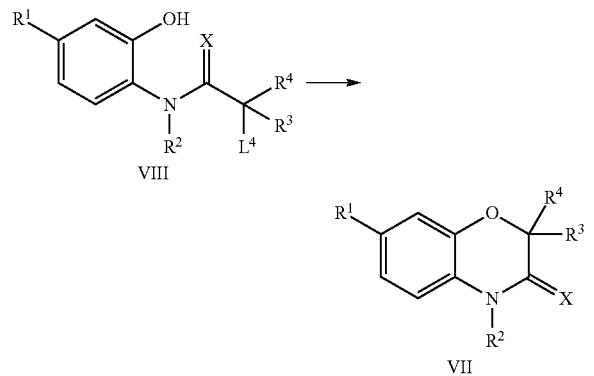

The cyclisation of the acetamide VIII is usually carried out at from 0° C. to the boiling point of the reaction mixture, preferably at from 0° C. to 140° C., particularly preferably at from 20° C. to 120° C., in an inert organic solvent in the presence of a base [WO 02/066471].

$L^4$ is halogen selected from Cl, Br, I; preferably Cl or Br; most preferably Cl, also most preferably Br.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, as well as dimethylsulfoxide.

It is also possible to use mixtures of the solvents mentioned.

Suitable bases are, in general Inorganic compounds such as alkali metal and alkaline earth metal hydroxides such as lithium hydroxide, sodium hydroxide, potassium hydroxide and calcium hydroxide, alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to 1,8-Diazabicyclo[5.4.0]undec-7-en (DBU).

The bases are generally employed in catalytic amounts, however they can also be employed in equimolar amounts, in excess or, if appropriate, be used as solvent.

Work up can be carried out in a known manner.

The acetamides VIII in turn can be obtained from the corresponding phenol IX:

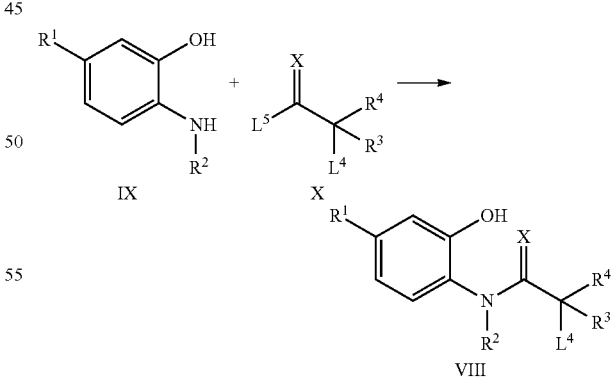

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

$L^4$ is halogen selected from Cl, Br, I; preferably Cl or Br; most preferably Cl, also most preferably Br.

$L^5$ is a known activating group for acylations, e.g. halogen or $C_1$-$C_6$-alkoxy, preferably Cl or $C_1$-$C_6$-alkoxy, most preferably Cl, $OCH_3$ or $OC_2H_5$.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide.

Particular preference is given to ethers such as diethyl ether, diisopropyl ether, tert.butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to tertiary amines such as trimethylamine, triethylamine, diisopropylethylamine and alkali metal and alkaline earth metal alkoxides such as sodium methoxide, sodium ethoxide, potassium ethoxide, The bases are generally employed in catalytic amounts, however they can also be employed in equimolar amounts, in excess or, if appropriate, be used as solvent.

Work up can be carried out in a known manner.

The phenols IX required for the preparation of the acetamides VIII are known from the literature [WO 02/066471] or they can be prepared in accordance with the literature cited and/or are commercially available.

The compounds X required for the preparation of the acetamides VIII are commercially available.

With regard to the educts mentioned for the preparation of the compounds of formula I, the variables mentioned in connection with the educts have the same meaning, preferably the preferred meaning as mentioned herein with regard to the respective variables in formula I.

The uracils of formula I are suitable as herbicides. They are suitable as such or as an appropriately formulated composition (herbicidal composition). As used in this application, the terms "formulated composition" and "herbicidal composition" are synonyms. The herbicidal compositions comprising the uracils of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the uracils of formula I or compositions comprising them can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. altissima, *Beta vulgaris* spec. rapa, *Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticum aestivum, Triticale, Triticum durum, Vicia faba, Vitis vinifera* and *Zea mays.*

Preferred crops are the following: *Arachis hypogaea, Beta vulgaris* spec. altissima, *Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*S. vulgare*), *Triticale, Triticum aestivum, Triticum durum, Vicia faba, Vitis vinifera* and *Zea mays.*

The uracils of formula I according to the invention can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties. Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glypho-sate and glufosinate, some of which are commercially available under the trade names RoundupReady® (glyphosate-tolerant, Monsanto, U.S.A.) and LibertyLink® (glufosinatetolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photo-rhab-dus spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are dis-closed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (*Coeloptera*), two-winged insects (*Diptera*), and moths (*Lepidoptera*) and to nematodes (*Nematoda*). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Her-*culex*® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars produ-cing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are, by the use of recombinant DNA techniques capable to synthesize one or more proteins to in-crease the resistance or tolerance of those plants to bacterial, viral or fungal pathogens. Examples of such, proteins are the so-called "pathogenesis-related proteins" (PR proteins, see, e.g. EP-A 392 225), plant disease resistance genes (e.g. potato culti-vars, which, express resistance genes acting against *Phytophthora infestans* derived from the Mexican wild potato *Solanum bulbocastanum*) or T4-lyso-zyme (e.g. potato cultivars capable of synthesizing these proteins with increased resistance against bacteria such as *Erwinia amylvora*). The methods for producing such genetically modi-fied plants are generally known to the person skilled, in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce healthpromoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The uracils of formula I according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding.

Suitable are for example crop plants, preferably corn, wheat, sunflower, sugarcane, cotton, rice, canola, oilseed rape or soybeans, which crops are resistant to herbicidal PPO inhibitors, or crop plants which, owing to introduction of the gene for Bt toxin by genetic modification, are resistant to attack by certain insects.

Furthermore, it has been found that the uracils of the formula I are also suitable for the defoliation and/or desiccation of plant parts, for which crop plants such as cotton, potato, oilseed rape, sunflower, soybean or field beans, in particular cotton, are suitable. In this regard there have been found compositions for the desiccation and/or defoliation of plants, processes for preparing these compositions and methods for desiccating and/or defoliating plants using the uracils of the formula I.

As desiccants, the uracils of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The uracils of formula I, or the herbicidal compositions comprising the uracils of formula I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one uracils of the formula I and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high, viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhard).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from; Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments, and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers. Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or concomitant grinding the active ingredients together with a solid carrier. Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the uracils of the formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the uracils of the formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the uracils of formula I according to the present invention the active ingredients, e.g. the uracils of formula I, are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The uracils of formula I according to the present invention can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The uracils of the formula I or the herbicidal compositions comprising them can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (postdirected, lay-by).

In a further embodiment, the uracils of the formula I or the herbicidal compositions can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting)

based on the uracils of the formula I according to the invention or the compositions prepared therefrom. Here, the herbicidal compositions can be applied diluted or undiluted.

The term "seed" comprises seed of all types, such as for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The rates of application of the active uracils of formula I according to the present invention (total amount of uracil I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the uracils of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the uracils of formula I is 0.1 to 1000 g/ha, preferably) to 750 g/ha, more preferably 5 to 500 g/ha, of active substance.

To treat the seed, the uracils of formula I are generally employed in amounts of from 0.001 to 10 kg per 100 kg of seed.

To broaden the spectrum of action and to achieve synergistic effects, the uracils of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-uracils, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may be beneficial to apply the uracils of the formula I alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non phytotoxic oils and oil concentrates may also be added.

The further herbicidal active component B is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;
b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

Preference is given to those compositions according to the present invention comprising at least one herbicide B selected from herbicides of class b2, b3, b4, b5, b6, b9 and b10.

Particular preference is given to those compositions according to the present invention which comprise at least one herbicide B selected from the herbicides of class b4, b6 and b10.

Examples of herbicides B which can be used in combination with the uracils of the formula I according, to the present invention are:

b1) from the group of the lipid biosynthesis inhibitors:
ACC-herbicides such as alloxydim, alloxydim-sodium, butroxydim clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-Ptefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuronmethyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8) and sulfonylaminocarbonyltriazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uracils such as bromacil, lenacil and terbacil, and bentazon and bentazon-sodium, pyridate, pyridafol, pentanochlor and propanil and inhibitors of the photosystem I such as diquat, diquatdibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione and 2-(2,2,7-Trifluoro-3-oxo-4-prop-2-ynyl-3,4-dihydro-2H-benzo[1,4]oxazin-6-yl)-4,5,6,7-tetrahydroisoindole-1,3-dione;

b5) from the group of the bleacher herbicides:
PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole, clomazone and flumeturon;

b6) from the group of the EPSP synthase inhibitors:
glyphosate, glyphosate-isopropylammonium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitose inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronilide and napropamide, tetrazolinones such fentrazamide, and other herbicides such as anilofos, cafenstrole, fenoxasulfone, ipfencarbazone, piperophos, pyroxasulfone and isoxazoline compounds of the formula II

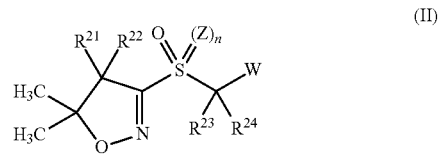

wherein $R^{21}$, $R^{22}$, $R^{23}$, $R^{24}$, W, Z and n have the following meanings:
$R^{21}$, $R^{22}$, $R^{23}$, $R^{24}$ independently of one another hydrogen, halogen or $C_1$-$C_4$-alkyl;
W phenyl or monocyclic 5-, 6-, 7-, 8-, 9- or 10-membered heterocyclyl containing, in addition to carbon ring members one two or three same or different heteroatoms selected from oxygen, nitrogen and sulfur as ring members, wherein phenyl and heterocyclyl are unsubstituted or carry 1, 2 or 3 substituents RYY selected from halogen, $C_1$-$C_4$-alkyl, $C_1$-$C_4$-alkoxy, $C_1$-$C_4$-haloalkyl and $C_1$-$C_4$-haloalkoxy;
preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$;
Z oxygen or NH; and
n zero or one;
among the isoxazoline compounds of the formula II, preference is given to isoxazoline compounds of the formula II, wherein
$R^{21}$, $R^{22}$, $R^{23}$, $R^{24}$ independently of one another are H, F, Cl or methyl;
Z is oxygen;
n is 0 or 1; and
W is phenyl, pyrazolyl or 1,2,3-triazolyl, wherein the three last-mentioned radicals are unsubstituted or carry one, two or three substituents RYY, especially one of the following radicals

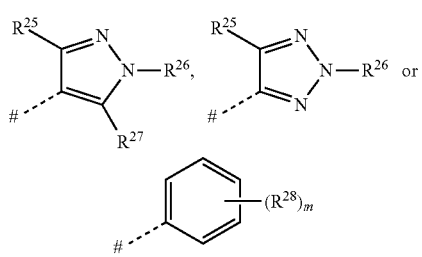

wherein
$R^{22}$ is halogen, $C_1$-$C_4$-alkyl or $C_1$-$C_4$-haloalkyl;
$R^{26}$ is $C_1$-$C_4$-alkyl;
$R^{27}$ is halogen, $C_1$-$C_4$-alkoxy or $C_1$-$C_4$-haloalkoxy;
$R^{28}$ is halogen, $C_1$-$C_4$-alkyl, $C_1$-$C_4$-haloalkyl or $C_1$-$C_4$-haloalkoxy;
m is 0, 1, 2 or 3; and
# denotes the point of attachment to the group $CR^{23}R^{24}$;
among the isoxazoline compounds of the formula II, particular preference is given to those isoxazoline compounds of the formula II, wherein
$R^{21}$ is hydrogen;
$R^{22}$ is fluorine;
$R^{23}$ is hydrogen or fluorine;
$R^{24}$ is hydrogen or fluorine;
W is one of the radicals of the formulae $W^1$, $W^2$, $W^3$ or $W^4$

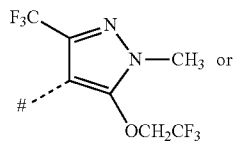

W$^1$

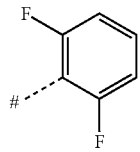

W$^2$

-continued

W$^3$

W$^4$ wherein # denotes the point of attachment to the group $CR^{13}R^{14}$;
Z is oxygen;
n is zero or 1, in particular 1; and
among these, especially preferred are the isoxazoline compounds of the formulae II.1, II.2, II.3, II.4, II.5, II.6, II.7, II.8 and II.9

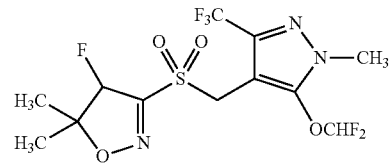

II.1

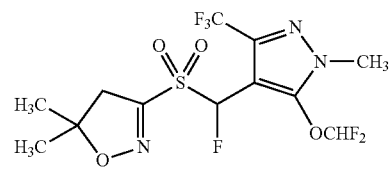

II.2

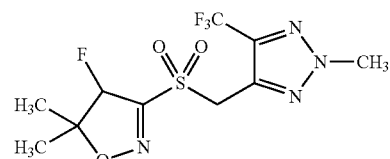

II.3

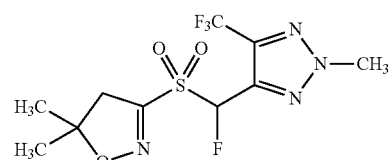

II.4

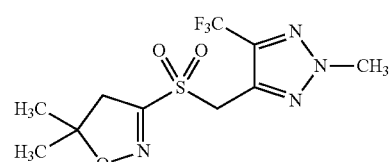

II.5

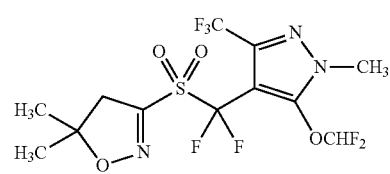

II.6

-continued

II.7

II.8

II.9 the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and *oxy*a-cetamides;

b11) from the group of the cellulose biosynthesis inhibitors: chlorthiamid, dichlobenil, flupoxam, isoxaben, 1-Cyclohexyl-5-pentafluorphenyloxy-1$^4$-[1,2,4,6]thiatriazin-3-ylamine and piperazine compounds of formula III

III in which

A is phenyl or pyridyl where $R^a$ is attached in the ortho-position to the point of attachment of A to a carbon atom;

$R^a$ is CN, NO$_2$, C$_1$-C$_4$, D-C$_3$-C$_6$-cycloalkyl, C$_1$-C$_4$-alkoxy, C$_1$-C$_4$-haloalkoxy, O-D-C$_3$-C$_6$-cycloalkyl, S(O)$_q$R$^y$, C$_2$-C$_6$-alkenyl, D-C$_3$-C$_6$-cycloalkenyl, C$_3$-C$_6$-alkenyloxy, C$_2$-C$_6$-alkynyl, C$_3$-C$_6$-alkynyloxy, NR$^A$R$^B$, triC$_1$-C$_4$-alkylsilyl, D-C(=O)—R$^{a1}$, D-P(=O)(R$^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups R$^{aa}$ and/or R$^{a1}$, and, if R$^a$ is attached to a carbon atom, additionally halogen;

R$^y$ is C$_1$-C$_6$-alkyl, C$_3$-C$_4$-alkenyl, C$_3$-C$_4$-alkynyl, NR$^A$R$^B$ or C$_1$-C$_4$-haloalkyl and q is 0, 1 or 2;

R$^A$,R$^B$ independently of one another are hydrogen, C$_1$-C$_6$-alkyl, C$_3$-C$_6$-alkenyl and C$_3$-C$_6$-alkynyl; together with the nitrogen atom to which they are attached, R$^A$,R$^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups R$^{aa}$;

D is a covalent bond, C$_1$-C$_4$-alkylene, C$_2$-C$_6$-alkenyl or C$_2$-C$_6$-alkynyl;

R$^{a1}$ is hydrogen, OH, C$_1$-C$_8$-Alkyl, C$_1$-C$_4$-haloalkyl, C$_3$-C$_6$-cycloalkyl, C$_2$-C$_8$-alkenyl, C$_6$-C$_6$-cycloalkenyl, C$_2$-C$_6$-alkynyl, C$_1$-C$_6$-alkoxy, C$_1$-C$_4$-haloalkoxy, C$_3$-C$_8$-alkenyloxy, C$_3$-C$_8$-alkynyloxy, NR$^A$R$^B$, C$_1$-C$_6$-alkoxyamino, C$_1$-C$_6$-alkylsulfonylamino, C$_1$-C$_6$-alkylaminosulfonylamino, [di-(C$_1$-C$_6$)alkylamino]sulfonylamino, C$_3$-C$_6$-alkenylamino, C$_3$-C$_6$-alkynylamino, N—(C$_2$-C$_6$-alkenyl)-N—(C$_1$-C$_6$-alkyl)amino, N—(C$_2$-C$_6$-alkynyl)-N—(C$_1$-C$_6$-alkyl)amino, N—(C$_1$-C$_6$-alkoxy)-N—(C$_1$-C$_6$-alkyl)amino, N—(C$_2$-C$_6$-alkenyl)-N—(C$_1$-C$_6$-alkoxy)amino, N—(C$_2$-C$_6$-alkynyl)-N—(C$_1$-C$_6$-alkoxy)amino, C$_1$-C$_6$-alkylsulfonyl, tri-C$_1$-C$_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups R$^{aa}$;

R$^{aa}$ is halogen, OH, CN, NO$_2$, C$_1$-C$_4$-haloalkyl, C$_1$-C$_4$-alkoxy, C$_1$-C$_4$-haloalkoxy, S(O)$_q$R$^y$, D-C(=O)—R$^{a1}$ and tri-C$_1$-C$_4$-alkylsilyl;

R$^b$ independently of one another are hydrogen, CN, NO$_2$, halogen, C$_1$-C$_4$-alkyl, C$_1$-C$_4$ haloalkyl, C$_2$-C$_4$-alkenyl, C$_3$-C$_6$-alkynyl, C$_1$-C$_4$-alkoxy, C$_1$-C$_4$-haloalkoxy, benzyl or S(O)$_q$R$^y$, R$^b$ together with the group R$^a$ or R$^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by R$^{aa}$;

p is 0, 1, 2 or 3;

R$^{30}$ is hydrogen, OH, CN, C$_1$-C$_{12}$-alkyl, C$_3$-C$_{12}$-alkenyl, C$_3$-C$_{12}$-alkynyl, C$_1$-C$_4$-alkoxy, C$_3$-C$_6$-cycloalkyl, C$_5$-C$_6$-cycloalkenyl, NR$^A$R$^B$, S(O)$_n$R$^y$, S(O)$_n$NR$^A$R$^B$, C(=O)R$^{40}$, CONR$^A$R$^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via D$^1$ and are unsubstituted or substituted by 1, 2, 3 or 4 groups R$^{aa}$, and also the following partially or fully R$^{aa}$-substituted groups: C$_1$-C$_4$-alkyl, C$_3$-C$_4$-alkenyl and C$_3$-C$_4$-alkynyl;

R$^{40}$ is hydrogen, C$_1$-C$_4$-alkyl, C$_1$-C$_4$-alkoxy or C$_1$-C$_4$-haloalkoxy;

D$^1$ is carbonyl or a group D;

where in groups R$^{15}$, R$^a$ and their sub-substituents the carbon chains and/or the cyclic groups may carry 1, 2, 3 or 4 substituents R$^{aa}$ and/or R$^{a1}$;

R$^{31}$ is C$_1$-C$_4$-alkyl, C$_3$-C$_4$-alkenyl or C$_3$-C$_4$-alkynyl;

R$^{32}$ is OH, NH$_2$, C$_1$-C$_4$-alkyl, C$_3$-C$_6$-cycloalkyl, C$_3$-C$_6$-alkenyl, C$_3$-C$_6$-alkynyl, C$_1$-C$_4$-hydroxyalkyl, C$_1$-C$_4$-cyanoalkyl, C$_1$-C$_4$-haloalkyl, C$_1$-C$_4$-alkoxy-C$_1$-C$_4$-alkyl or C(=O)R$^{40}$;

R$^{33}$ is hydrogen, halogen, C$_1$-C$_4$-alkyl or C$_1$-C$_4$-haloalkyl, or R$^{33}$ and R$^{34}$ together are a covalent bond;

R$^{34}$, R$^{35}$, R$^{36}$, R$^{37}$ independently of one another are hydrogen, halogen, OH, CN, NO$_2$, C$_1$-C$_4$-haloalkyl, C$_2$-C$_6$- alkenyl, $C_2$-$C_6$-alkynyl, $C_1$-$C_4$-haloalkoxy, $C_3$-$C_6$-cycloalkyl, $C_3$-$C_6$-cycloalkenyl and $C_3$-$C_6$-cycloalkynyl;

$R^{38}$, $R^{39}$ independently of one another are hydrogen, halogen, OH, haloalkyl, $NR^A R^B$, $NR^A C(O)R^{41}$, CN, $NO_2$, $C_2$-$C_4$-alkenyl, $C_3$-$C_6$-alkynyl, $C_1$-$C_4$-alkoxy, $C_1$-$C_4$-haloalkoxy, O—$C(O)R^{41}$, phenoxy or benzyloxy, wherein in groups $R^{38}$ and $R^{39}$ the carbon chains and/or the cyclic groups may carry 1, 2, 3 or 4 substituents $R^{aa}$;

$R^{41}$ is $C_1$-$C_4$-alkyl or $NR^A R^B$;

among the piperazine compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^A R^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{30}$ is hydrogen, $C_1$-$C_{12}$-alkyl, $C_3$-$C_{12}$-alkenyl, $C_3$-$C_{12}$-alkynyl, $C_1$-$C_4$-alkoxy or C(=O)$R^{40}$;

$R^{40}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{30}$, $R^a$ and their sub-substituents the carbon chains and/or the cyclic groups may carry 1, 2, 3 or 4 substituents $R^{aa}$ and/or $R^{a1}$;

$R^{31}$ is $C_1$-$C_4$-alkyl;

$R^{32}$ is OH, $NH_2$, $C_1$-$C_4$-alkyl, $C_3$-$C_6$-cycloalkyl, $C_1$-$C_4$-haloalkyl or C(=O)$R^{25}$;

$R^{33}$ is hydrogen, or $R^{33}$ and $R^{34}$ together are a covalent bond;

$R^{34}$, $R^{35}$, $R^{36}$, $R^{37}$ independently of one another are hydrogen;

$R^{38}$, $R^{39}$ independently of one another are hydrogen, halogen or OH;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorpropand its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecopropand its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors:
diflufenzopyr, diflufenzopyrsodium, naptalam and naptalam-sodium;

b15) from the group of the other herbicides: bromobutide, chlorflurenol, chlorflurenolmethyl, cinmethylin, cumyluron, dalapon, dazomet, difenzoquat, difenzoquatmetilsulfate, dimethipin, DSMA, dynnron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Moreover, it may be useful to apply the uracils of the formula I in combination with safeners. Safeners are chemical compounds which prevent or reduce damage on useful plants without having a major impact on the herbicidal action of the uracils of the formula I towards unwanted plants. They can be applied either before sowings (e.g. on seed treatments, shoots or seedlings) or in the pre-emergence application or post-emergence application of the useful plant. The safeners and the uracils of the formula I can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alphaoximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The active compounds of groups b1) to b15) and the safeners C are known herbicides and safeners, see, for example, The Compendium of Pesticide Common Names (http.//www.alanwood.net/pesticides/); B. Hock, C. Fedtke, R. R. Schmidt, Herbizide [Herbicides], Georg Thieme Verlag, Stuttgart, 1995. Further herbicidal active compounds are known from WO 96/26202, WO 97/41116, WO 97/41117, WO 97/41118, WO 01/83459 and WO 2008/074991 and from W. Kramer et al. (ed.) "Modern Crop Protection Compounds", Vol. 1, Wiley VCH, 2007 and the literature quoted therein.

The invention also relates to compositions in the form of a crop protection composition formulated as a 1-component composition comprising an active compound combination comprising at least one uracil of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one uracil of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.

Particularly preferred herbicides Bare the herbicides B as defined above; in particular the herbicides B.1-B.143 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-P-ethyl |
| B.6 | metamifop |
| B.7 | pinoxaden |
| B.8 | profoxydim |
| B.9 | sethoxydim |
| B.10 | tepraloxydim |
| B.11 | tralkoxydim |
| B.12 | esprocarb |
| B.13 | ethofumesate |
| B.14 | molinate |
| B.15 | prosulfocarb |
| B.16 | thiobencarb |
| B.17 | triallate |
| B.18 | bensulfuron-methyl |
| B.19 | bispyribac-sodium |
| B.20 | cloransulam |
| B.21 | chlorsulfuron |
| B.22 | clorimuron |
| B.23 | cyclosulfamuron |
| B.24 | diclosulam |
| B.25 | florasulam |
| B.26 | flumetsulam |
| B.27 | flupyrsulfuron-methyl-sodium |
| B.28 | foramsulfuron |
| B.29 | imazamox |
| B.30 | imazapic |
| B.31 | imazapyr |
| B.32 | imazaquin |
| B.33 | imazethapyr |
| B.34 | imazosulfuron |
| B.35 | iodosulfuron-methyl-sodium |
| B.36 | mesosulfuron |
| B.37 | metazosulfuron |
| B.38 | metsulfuron |
| B.39 | metosulam |
| B.40 | nicosulfuron |
| B.41 | penoxsulam |
| B.42 | propoxycarbazon-sodium |
| B.43 | pyrazosulfuron-ethyl |
| B.44 | pyribenzoxim |
| B.45 | pyriftalid |
| B.46 | pyroxsulam |
| B.47 | rimsulfuron |
| B.48 | sulfosulfuron |
| B.49 | thiencarbazone-methyl |
| B.50 | thifensulfuron |
| B.51 | tribenuron |
| B.52 | tritosulfuron |
| B.53 | ametryne |
| B.54 | atrazine |
| B.55 | bentazon |
| B.56 | bromoxynil |
| B.57 | diuron |
| B.58 | fluometuron |
| B.59 | hexazinone |
| B.60 | isoproturon |
| B.61 | linuron |
| B.62 | metamitron |
| B.63 | metribuzin |
| B.64 | propanil |
| B.65 | simazin |
| B.66 | terbuthylazine |
| B.67 | terbutryn |
| B.68 | paraquat-dichloride |
| B.69 | acifluorfen |
| B.70 | butafenacil |
| B.71 | carfentrazone-ethyl |
| B.72 | flumioxazin |
| B.73 | fomesafen |

TABLE B-continued

| | Herbicide B |
|---|---|
| B.74 | oxadiargyl |
| B.75 | oxyfluorfen |
| B.76 | saflufenacil |
| B.77 | sulfentrazone |
| B.78 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.79 | 3-[7-fluoro-3-oxo-4-(prop-2-ynyl)-3,4-dihydro-2H-benzo[1,4]-oxazin-6-yl]-1,5-dimethyl-6-thioxo-[1,3,5]triazinan-2,4-dione |
| B.80 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione |
| B.81 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.82 | benzobicyclon |
| B.83 | clomazone |
| B.84 | diflufenican |
| B.85 | flurochloridone |
| B.86 | isoxaflutole |
| B.87 | mesotrione |
| B.88 | norflurazone |
| B.89 | picolinafen |
| B.90 | sulcotrione |
| B.91 | tefuryltrione |
| B.92 | tembotrione |
| B.93 | topramezone |
| B.94 | bicyclopyrone |
| B.95 | amitrole |
| B.96 | fluometuron |
| B.97 | glyphosate |
| B.98 | glyphosate-isopropylammonium |
| B.99 | glyphosate-trimesium (sulfosate) |
| B.100 | glufosinate |
| B.101 | glufosinate-P |
| B.102 | glufosinate-ammonium |
| B.103 | pendimethalin |
| B.104 | trifluralin |
| B.105 | acetochlor |
| B.106 | butachlor |
| B.107 | cafenstrole |
| B.108 | dimethenamid-P |
| B.109 | fentrazamide |
| B.110 | flufenacet |
| B.111 | mefenacet |
| B.112 | metazachlor |
| B.113 | metolachlor |
| B.114 | S-metolachlor |
| B.115 | pretilachlor |
| B.116 | fenoxasulfone |
| B.117 | isoxaben |
| B.118 | pyroxasulfone |
| B.119 | 2,4-D |
| B.120 | aminopyralid |
| B.121 | clopyralid |
| B.122 | dicamba |
| B.123 | fluroxypyr-meptyl |
| B.124 | MCPA |
| B.125 | quinclorac |
| B.126 | quinmerac |
| B.127 | aminocyclopyrachlor |
| B.128 | diflufenzopyr |
| B.129 | diflufenzopyr-sodium |
| B.130 | dymron |
| B.131 | indanofan |
| B.132 | indaziflam |
| B.133 | oxaziclomefone |
| B.134 | triaziflam |
| B.135 | II.1 |
| B.136 | II.2 |
| B.137 | II.3 |
| B.138 | II.4 |
| B.139 | II.5 |
| B.140 | II.6 |
| B.141 | II.7 |
| B.142 | II.8 |
| B.143 | II.9 |

Particularly preferred safeners C, which, as component C, are constituent of the composition according to the invention are the safeners C as defined above; in particular the safeners C.1-C.12 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphthalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloroacetyl)-1,3-oxazolidine (R-29148, CAS 52836-31-4) |

The weight ratios of the individual components in the preferred mixtures mentioned below are within the limits given above, in particular within the preferred limits.

Particularly preferred are the compositions mentioned below comprising the uracils of formula I as defined and the substance(s) as defined in the respective row of table 1; especially preferred comprising as only herbicidal active compounds the uracils of formula I as defined and the substance(s) as defined in the respective row of table 1; most preferably comprising as only active compounds the uracils of formula I as defined and the substance(s) as defined in the respective row of table 1.

Particularly preferred are compositions 1.1 to 1.1871 comprising the uracil Ia48 and the substance(s) as defined in the respective row of table 1:

TABLE 1

(compositions 1.1 to 1.1871):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |

TABLE 1-continued (compositions 1.1 to 1.1871):

| comp. no. | herbicide B | safener C |
|---|---|---|
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.1 | C.1 |
| 1.145 | B.2 | C.1 |
| 1.146 | B.3 | C.1 |
| 1.147 | B.4 | C.1 |
| 1.148 | B.5 | C.1 |
| 1.149 | B.6 | C.1 |
| 1.150 | B.7 | C.1 |
| 1.151 | B.8 | C.1 |
| 1.152 | B.9 | C.1 |
| 1.153 | B.10 | C.1 |
| 1.154 | B.11 | C.1 |
| 1.155 | B.12 | C.1 |
| 1.156 | B.13 | C.1 |
| 1.157 | B.14 | C.1 |
| 1.158 | B.15 | C.1 |
| 1.159 | B.16 | C.1 |
| 1.160 | B.17 | C.1 |
| 1.161 | B.18 | C.1 |
| 1.162 | B.19 | C.1 |
| 1.163 | B.20 | C.1 |
| 1.164 | B.21 | C.1 |
| 1.165 | B.22 | C.1 |
| 1.166 | B.23 | C.1 |

TABLE 1-continued (compositions 1.1 to 1.1871):

| comp. no. | herbicide B | safener C |
|---|---|---|
| 1.167 | B.24 | C.1 |
| 1.168 | B.25 | C.1 |
| 1.169 | B.26 | C.1 |
| 1.170 | B.27 | C.1 |
| 1.171 | B.28 | C.1 |
| 1.172 | B.29 | C.1 |
| 1.173 | B.30 | C.1 |
| 1.174 | B.31 | C.1 |
| 1.175 | B.32 | C.1 |
| 1.176 | B.33 | C.1 |
| 1.177 | B.34 | C.1 |
| 1.178 | B.35 | C.1 |
| 1.179 | B.36 | C.1 |
| 1.180 | B.37 | C.1 |
| 1.181 | B.38 | C.1 |
| 1.182 | B.39 | C.1 |
| 1.183 | B.40 | C.1 |
| 1.184 | B.41 | C.1 |
| 1.185 | B.42 | C.1 |
| 1.186 | B.43 | C.1 |
| 1.187 | B.44 | C.1 |
| 1.188 | B.45 | C.1 |
| 1.189 | B.46 | C.1 |
| 1.190 | B.47 | C.1 |
| 1.191 | B.48 | C.1 |
| 1.192 | B.49 | C.1 |
| 1.193 | B.50 | C.1 |
| 1.194 | B.51 | C.1 |
| 1.195 | B.52 | C.1 |
| 1.196 | B.53 | C.1 |
| 1.197 | B.54 | C.1 |
| 1.198 | B.55 | C.1 |
| 1.199 | B.56 | C.1 |
| 1.200 | B.57 | C.1 |
| 1.201 | B.58. | C.1 |
| 1.202 | B.59 | C.1 |
| 1.203 | B.60 | C.1 |
| 1.204 | B.61 | C.1 |
| 1.205 | B.62 | C.1 |
| 1.206 | B.63 | C.1 |
| 1.207 | B.64 | C.1 |
| 1.208 | B.65 | C.1 |
| 1.209 | B.66 | C.1 |
| 1.210 | B.67 | C.1 |
| 1.211 | B.68 | C.1 |
| 1.212 | B.69 | C.1 |
| 1.213 | B.70 | C.1 |
| 1.214 | B.71 | C.1 |
| 1.215 | B.72 | C.1 |
| 1.216 | B.73 | C.1 |
| 1.217 | B.74 | C.1 |
| 1.218 | B.75 | C.1 |
| 1.219 | B.76 | C.1 |
| 1.220 | B.77 | C.1 |
| 1.221 | B.78 | C.1 |
| 1.222 | B.79 | C.1 |
| 1.223 | B.80 | C.1 |
| 1.224 | B.81 | C.1 |
| 1.225 | B.82 | C.1 |
| 1.226 | B.83 | C.1 |
| 1.227 | B.84 | C.1 |
| 1.228 | B.85 | C.1 |
| 1.229 | B.86 | C.1 |
| 1.230 | B.87 | C.1 |
| 1.231 | B.88 | C.1 |
| 1.232 | B.89 | C.1 |
| 1.233 | B.90 | C.1 |
| 1.234 | B.91 | C.1 |
| 1.235 | B.92 | C.1 |
| 1.236 | B.93 | C.1 |
| 1.237 | B.94 | C.1 |
| 1.238 | B.95 | C.1 |
| 1.239 | B.96 | C.1 |
| 1.240 | B.97 | C.1 |
| 1.241 | B.98 | C.1 |
| 1.242 | B.99 | C.1 |
| 1.243 | B.100 | C.1 |
| 1.244 | B.101 | C.1 |
| 1.245 | B.102 | C.1 |
| 1.246 | B.103 | C.1 |
| 1.247 | B.104 | C.1 |
| 1.248 | B.105 | C.1 |
| 1.249 | B.106 | C.1 |
| 1.250 | B.107 | C.1 |
| 1.251 | B.108 | C.1 |
| 1.252 | B.109 | C.1 |
| 1.253 | B.110 | C.1 |
| 1.254 | B.111 | C.1 |
| 1.255 | B.112 | C.1 |
| 1.256 | B.113 | C.1 |
| 1.257 | B.114 | C.1 |
| 1.258 | B.115 | C.1 |
| 1.259 | B.116 | C.1 |
| 1.260 | B.117 | C.1 |
| 1.261 | B.118 | C.1 |
| 1.262 | B.119 | C.1 |
| 1.263 | B.120 | C.1 |
| 1.264 | B.121 | C.1 |
| 1.265 | B.122 | C.1 |
| 1.266 | B.123 | C.1 |
| 1.267 | B.124 | C.1 |
| 1.268 | B.125 | C.1 |
| 1.269 | B.126 | C.1 |
| 1.270 | B.127 | C.1 |
| 1.271 | B.128 | C.1 |
| 1.272 | B.129 | C.1 |
| 1.273 | B.130 | C.1 |
| 1.274 | B.131 | C.1 |
| 1.275 | B.132 | C.1 |
| 1.276 | B.133 | C.1 |
| 1.277 | B.134 | C.1 |
| 1.278 | B.135 | C.1 |
| 1.279 | B.136 | C.1 |
| 1.280 | B.137 | C.1 |
| 1.281 | B.138 | C.1 |
| 1.282 | B.139 | C.1 |
| 1.283 | B.140 | C.1 |
| 1.284 | B.141 | C.1 |
| 1.285 | B.142 | C.1 |
| 1.286 | B.143 | C.1 |
| 1.287 | B.1 | C.2 |
| 1.288 | B.2 | C.2 |
| 1.289 | B.3 | C.2 |
| 1.290 | B.4 | C.2 |
| 1.291 | B.5 | C.2 |
| 1.292 | B.6 | C.2 |
| 1.293 | B.7 | C.2 |
| 1.294 | B.8 | C.2 |
| 1.295 | B.9 | C.2 |
| 1.296 | B.10 | C.2 |
| 1.297 | B.11 | C.2 |
| 1.298 | B.12 | C.2 |
| 1.299 | B.13 | C.2 |
| 1.300 | B.14 | C.2 |
| 1.301 | B.15 | C.2 |
| 1.302 | B.16 | C.2 |
| 1.303 | B.17 | C.2 |
| 1.304 | B.18 | C.2 |
| 1.305 | B.19 | C.2 |
| 1.306 | B.20 | C.2 |
| 1.307 | B.21 | C.2 |
| 1.308 | B.22 | C.2 |
| 1.309 | B.23 | C.2 |
| 1.310 | B.24 | C.2 |
| 1.311 | B.25 | C.2 |
| 1.312 | B.26 | C.2 |
| 1.313 | B.27 | C.2 |
| 1.314 | B.28 | C.2 |
| 1.315 | B.29 | C.2 |
| 1.316 | B.30 | C.2 |

TABLE 1-continued (compositions 1.1 to 1.1871):

| comp. no. | herbicide B | safener C |
|---|---|---|
| 1.317 | B.31 | C.2 |
| 1.318 | B.32 | C.2 |
| 1.319 | B.33 | C.2 |
| 1.320 | B.34 | C.2 |
| 1.321 | B.35 | C.2 |
| 1.322 | B.36 | C.2 |
| 1.323 | B.37 | C.2 |
| 1.324 | B.38 | C.2 |
| 1.325 | B.39 | C.2 |
| 1.326 | B.40 | C.2 |
| 1.327 | B.41 | C.2 |
| 1.328 | B.42 | C.2 |
| 1.329 | B.43 | C.2 |
| 1.330 | B.44 | C.2 |
| 1.331 | B.45 | C.2 |
| 1.332 | B.46 | C.2 |
| 1.333 | B.47 | C.2 |
| 1.334 | B.48 | C.2 |
| 1.335 | B.49 | C.2 |
| 1.336 | B.50 | C.2 |
| 1.337 | B.51 | C.2 |
| 1.338 | B.52 | C.2 |
| 1.339 | B.53 | C.2 |
| 1.340 | B.54 | C.2 |
| 1.341 | B.55 | C.2 |
| 1.342 | B.56 | C.2 |
| 1.343 | B.57 | C.2 |
| 1.344 | B.58 | C.2 |
| 1.345 | B.59 | C.2 |
| 1.346 | B.60 | C.2 |
| 1.347 | B.61 | C.2 |
| 1.348 | B.62 | C.2 |
| 1.349 | B.63 | C.2 |
| 1.350 | B.64 | C.2 |
| 1.351 | B.65 | C.2 |
| 1.352 | B.66 | C.2 |
| 1.353 | B.67 | C.2 |
| 1.354 | B.68 | C.2 |
| 1.355 | B.69 | C.2 |
| 1.356 | B.70 | C.2 |
| 1.357 | B.71 | C.2 |
| 1.358 | B.72 | C.2 |
| 1.359 | B.73 | C.2 |
| 1.360 | B.74 | C.2 |
| 1.361 | B.75 | C.2 |
| 1.362 | B.76 | C.2 |
| 1.363 | B.77 | C.2 |
| 1.364 | B.78 | C.2 |
| 1.365 | B.79 | C.2 |
| 1.366 | B.80 | C.2 |
| 1.367 | B.81 | C.2 |
| 1.368 | B.82 | C.2 |
| 1.369 | B.83 | C.2 |
| 1.370 | B.84 | C.2 |
| 1.371 | B.85 | C.2 |
| 1.372 | B.86 | C.2 |
| 1.373 | B.87 | C.2 |
| 1.374 | B.88 | C.2 |
| 1.375 | B.89 | C.2 |
| 1.376 | B.90 | C.2 |
| 1.377 | B.91 | C.2 |
| 1.378 | B.92 | C.2 |
| 1.379 | B.93 | C.2 |
| 1.380 | B.94 | C.2 |
| 1.381 | B.95 | C.2 |
| 1.382 | B.96 | C.2 |
| 1.383 | B.97 | C.2 |
| 1.384 | B.98 | C.2 |
| 1.385 | B.99 | C.2 |
| 1.386 | B.100 | C.2 |
| 1.387 | B.101 | C.2 |
| 1.388 | B.102 | C.2 |
| 1.389 | B.103 | C.2 |
| 1.390 | B.104 | C.2 |
| 1.391 | B.105 | C.2 |
| 1.392 | B.106 | C.2 |
| 1.393 | B.107 | C.2 |
| 1.394 | B.108 | C.2 |
| 1.395 | B.109 | C.2 |
| 1.396 | B.110 | C.2 |
| 1.397 | B.111 | C.2 |
| 1.398 | B.112 | C.2 |
| 1.399 | B.113 | C.2 |
| 1.400 | B.114 | C.2 |
| 1.401 | B.115 | C.2 |
| 1.402 | B.116 | C.2 |
| 1.403 | B.117 | C.2 |
| 1.404 | B.118 | C.2 |
| 1.405 | B.119 | C.2 |
| 1.406 | B.120 | C.2 |
| 1.407 | B.121 | C.2 |
| 1.408 | B.122 | C.2 |
| 1.409 | B.123 | C.2 |
| 1.410 | B.124 | C.2 |
| 1.411 | B.125 | C.2 |
| 1.412 | B.126 | C.2 |
| 1.413 | B.127 | C.2 |
| 1.414 | B.128 | C.2 |
| 1.415 | B.129 | C.2 |
| 1.416 | B.130 | C.2 |
| 1.417 | B.131 | C.2 |
| 1.418 | B.132 | C.2 |
| 1.419 | B.133 | C.2 |
| 1.420 | B.134 | C.2 |
| 1.421 | B.135 | C.2 |
| 1.422 | B.136 | C.2 |
| 1.423 | B.137 | C.2 |
| 1.424 | B.138 | C.2 |
| 1.425 | B.139 | C.2 |
| 1.426 | B.140 | C.2 |
| 1.427 | B.141 | C.2 |
| 1.428 | B.142 | C.2 |
| 1.429 | B.143 | C.2 |
| 1.430 | B.1 | C.3 |
| 1.431 | B.2 | C.3 |
| 1.432 | B.3 | C.3 |
| 1.433 | B.4 | C.3 |
| 1.434 | B.5 | C.3 |
| 1.435 | B.6 | C.3 |
| 1.436 | B.7 | C.3 |
| 1.437 | B.8 | C.3 |
| 1.438 | B.9 | C.3 |
| 1.439 | B.10 | C.3 |
| 1.440 | B.11 | C.3 |
| 1.441 | B.12 | C.3 |
| 1.442 | B.13 | C.3 |
| 1.443 | B.14 | C.3 |
| 1.444 | B.15 | C.3 |
| 1.445 | B.16 | C.3 |
| 1.446 | B.17 | C.3 |
| 1.447 | B.18 | C.3 |
| 1.448 | B.19 | C.3 |
| 1.449 | B.20 | C.3 |
| 1.450 | B.21 | C.3 |
| 1.451 | B.22 | C.3 |
| 1.452 | B.23 | C.3 |
| 1.453 | B.24 | C.3 |
| 1.454 | B.25 | C.3 |
| 1.455 | B.26 | C.3 |
| 1.456 | B.27 | C.3 |
| 1.457 | B.28 | C.3 |
| 1.458 | B.29 | C.3 |
| 1.459 | B.30 | C.3 |
| 1.460 | B.31 | C.3 |
| 1.461 | B.32 | C.3 |
| 1.462 | B.33 | C.3 |
| 1.463 | B.34 | C.3 |
| 1.464 | B.35 | C.3 |
| 1.465 | B.36 | C.3 |
| 1.466 | B.37 | C.3 |

TABLE 1-continued (compositions 1.1 to 1.1871):

| comp. no. | herbicide B | safener C |
|---|---|---|
| 1.467 | B.38 | C.3 |
| 1.468 | B.39 | C.3 |
| 1.469 | B.40 | C.3 |
| 1.470 | B.41 | C.3 |
| 1.471 | B.42 | C.3 |
| 1.472 | B.43 | C.3 |
| 1.473 | B.44 | C.3 |
| 1.474 | B.45 | C.3 |
| 1.475 | B.46 | C.3 |
| 1.476 | B.47 | C.3 |
| 1.477 | B.48 | C.3 |
| 1.478 | B.49 | C.3 |
| 1.479 | B.50 | C.3 |
| 1.480 | B.51 | C.3 |
| 1.481 | B.52 | C.3 |
| 1.482 | B.53 | C.3 |
| 1.483 | B.54 | C.3 |
| 1.484 | B.55 | C.3 |
| 1.485 | B.56 | C.3 |
| 1.486 | B.57 | C.3 |
| 1.487 | B.58 | C.3 |
| 1.488 | B.59 | C.3 |
| 1.489 | B.60 | C.3 |
| 1.490 | B.61 | C.3 |
| 1.491 | B.62 | C.3 |
| 1.492 | B.63 | C.3 |
| 1.493 | B.64 | C.3 |
| 1.494 | B.65 | C.3 |
| 1.495 | B.66 | C.3 |
| 1.496 | B.67 | C.3 |
| 1.497 | B.68 | C.3 |
| 1.498 | B.69 | C.3 |
| 1.499 | B.70 | C.3 |
| 1.500 | B.71 | C.3 |
| 1.501 | B.72 | C.3 |
| 1.502 | B.73 | C.3 |
| 1.503 | B.74 | C.3 |
| 1.504 | B.75 | C.3 |
| 1.505 | B.76 | C.3 |
| 1.506 | B.77 | C.3 |
| 1.507 | B.78 | C.3 |
| 1.508 | B.79 | C.3 |
| 1.509 | B.80 | C.3 |
| 1.510 | B.81 | C.3 |
| 1.511 | B.82 | C.3 |
| 1.512 | B.83 | C.3 |
| 1.513 | B.84 | C.3 |
| 1.514 | B.85 | C.3 |
| 1.515 | B.86 | C.3 |
| 1.516 | B.87 | C.3 |
| 1.517 | B.88 | C.3 |
| 1.518 | B.89 | C.3 |
| 1.519 | B.90 | C.3 |
| 1.520 | B.91 | C.3 |
| 1.521 | B.92 | C.3 |
| 1.522 | B.93 | C.3 |
| 1.523 | B.94 | C.3 |
| 1.524 | B.95 | C.3 |
| 1.525 | B.96 | C.3 |
| 1.526 | B.97 | C.3 |
| 1.527 | B.98 | C.3 |
| 1.528 | B.99 | C.3 |
| 1.529 | B.100 | C.3 |
| 1.530 | B.101 | C.3 |
| 1.531 | B.102 | C.3 |
| 1.532 | B.103 | C.3 |
| 1.533 | B.104 | C.3 |
| 1.534 | B.105 | C.3 |
| 1.535 | B.106 | C.3 |
| 1.536 | B.107 | C.3 |
| 1.537 | B.108 | C.3 |
| 1.538 | B.109 | C.3 |
| 1.539 | B.110 | C.3 |
| 1.540 | B.111 | C.3 |
| 1.541 | B.112 | C.3 |
| 1.542 | B.113 | C.3 |
| 1.543 | B.114 | C.3 |
| 1.544 | B.115 | C.3 |
| 1.545 | B.116 | C.3 |
| 1.546 | B.117 | C.3 |
| 1.547 | B.118 | C.3 |
| 1.548 | B.119 | C.3 |
| 1.549 | B.120 | C.3 |
| 1.550 | B.121 | C.3 |
| 1.551 | B.122 | C.3 |
| 1.552 | B.123 | C.3 |
| 1.553 | B.124 | C.3 |
| 1.554 | B.125 | C.3 |
| 1.555 | B.126 | C.3 |
| 1.556 | B.127 | C.3 |
| 1.557 | B.128 | C.3 |
| 1.558 | B.129 | C.3 |
| 1.559 | B.130 | C.3 |
| 1.560 | B.131 | C.3 |
| 1.561 | B.132 | C.3 |
| 1.562 | B.133 | C.3 |
| 1.563 | B.134 | C.3 |
| 1.564 | B.135 | C.3 |
| 1.565 | B.136 | C.3 |
| 1.566 | B.137 | C.3 |
| 1.567 | B.138 | C.3 |
| 1.568 | B.139 | C.3 |
| 1.569 | B.140 | C.3 |
| 1.570 | B.141 | C.3 |
| 1.571 | B.142 | C.3 |
| 1.572 | B.143 | C.3 |
| 1.573 | B.1 | C.4 |
| 1.574 | B.2 | C.4 |
| 1.575 | B.3 | C.4 |
| 1.576 | B.4 | C.4 |
| 1.577 | B.5 | C.4 |
| 1.578 | B.6 | C.4 |
| 1.579 | B.7 | C.4 |
| 1.580 | B.8 | C.4 |
| 1.581 | B.9 | C.4 |
| 1.582 | B.10 | C.4 |
| 1.583 | B.11 | C.4 |
| 1.584 | B.12 | C.4 |
| 1.585 | B.13 | C.4 |
| 1.586 | B.14 | C.4 |
| 1.587 | B.15 | C.4 |
| 1.588 | B.16 | C.4 |
| 1.589 | B.17 | C.4 |
| 1.590 | B.18 | C.4 |
| 1.591 | B.19 | C.4 |
| 1.592 | B.20 | C.4 |
| 1.593 | B.21 | C.4 |
| 1.594 | B.22 | C.4 |
| 1.595 | B.23 | C.4 |
| 1.596 | B.24 | C.4 |
| 1.597 | B.25 | C.4 |
| 1.598 | B.26 | C.4 |
| 1.599 | B.27 | C.4 |
| 1.600 | B.28 | C.4 |
| 1.601 | B.29 | C.4 |
| 1.602 | B.30 | C.4 |
| 1.603 | B.31 | C.4 |
| 1.604 | B.32 | C.4 |
| 1.605 | B.33 | C.4 |
| 1.606 | B.34 | C.4 |
| 1.607 | B.35 | C.4 |
| 1.608 | B.36 | C.4 |
| 1.609 | B.37 | C.4 |
| 1.610 | B.38 | C.4 |
| 1.611 | B.39 | C.4 |
| 1.612 | B.40 | C.4 |
| 1.613 | B.41 | C.4 |
| 1.614 | B.42 | C.4 |
| 1.615 | B.43 | C.4 |
| 1.616 | B.44 | C.4 |

TABLE 1-continued (compositions 1.1 to 1.1871):

| comp. no. | herbicide B | safener C |
|---|---|---|
| 1.617 | B.45 | C.4 |
| 1.618 | B.46 | C.4 |
| 1.619 | B.47 | C.4 |
| 1.620 | B.48 | C.4 |
| 1.621 | B.49 | C.4 |
| 1.622 | B.50 | C.4 |
| 1.623 | B.51 | C.4 |
| 1.624 | B.52 | C.4 |
| 1.625 | B.53 | C.4 |
| 1.626 | B.54 | C.4 |
| 1.627 | B.55 | C.4 |
| 1.628 | B.56 | C.4 |
| 1.629 | B.57 | C.4 |
| 1.630 | B.58 | C.4 |
| 1.631 | B.59 | C.4 |
| 1.632 | B.60 | C.4 |
| 1.633 | B.61 | C.4 |
| 1.634 | B.62 | C.4 |
| 1.635 | B.63 | C.4 |
| 1.636 | B.64 | C.4 |
| 1.637 | B.65 | C.4 |
| 1.638 | B.66 | C.4 |
| 1.639 | B.67 | C.4 |
| 1.640 | B.68 | C.4 |
| 1.641 | B.69 | C.4 |
| 1.642 | B.70 | C.4 |
| 1.643 | B.71 | C.4 |
| 1.644 | B.72 | C.4 |
| 1.645 | B.73 | C.4 |
| 1.646 | B.74 | C.4 |
| 1.647 | B.75 | C.4 |
| 1.648 | B.76 | C.4 |
| 1.649 | B.77 | C.4 |
| 1.650 | B.78 | C.4 |
| 1.651 | B.79 | C.4 |
| 1.652 | B.80 | C.4 |
| 1.653 | B.81 | C.4 |
| 1.654 | B.82 | C.4 |
| 1.655 | B.83 | C.4 |
| 1.656 | B.84 | C.4 |
| 1.657 | B.85 | C.4 |
| 1.658 | B.86 | C.4 |
| 1.659 | B.87 | C.4 |
| 1.660 | B.88 | C.4 |
| 1.661 | B.89 | C.4 |
| 1.662 | B.90 | C.4 |
| 1.663 | B.91 | C.4 |
| 1.664 | B.92 | C.4 |
| 1.665 | B.93 | C.4 |
| 1.666 | B.94 | C.4 |
| 1.667 | B.95 | C.4 |
| 1.668 | B.96 | C.4 |
| 1.669 | B.97 | C.4 |
| 1.670 | B.98 | C.4 |
| 1.671 | B.99 | C.4 |
| 1.672 | B.100 | C.4 |
| 1.673 | B.101 | C.4 |
| 1.674 | B.102 | C.4 |
| 1.675 | B.103 | C.4 |
| 1.676 | B.104 | C.4 |
| 1.677 | B.105 | C.4 |
| 1.678 | B.106 | C.4 |
| 1.679 | B.107 | C.4 |
| 1.680 | B.108 | C.4 |
| 1.681 | B.109 | C.4 |
| 1.682 | B.110 | C.4 |
| 1.683 | B.111 | C.4 |
| 1.684 | B.112 | C.4 |
| 1.685 | B.113 | C.4 |
| 1.686 | B.114 | C.4 |
| 1.687 | B.115 | C.4 |
| 1.688 | B.116 | C.4 |
| 1.689 | B.117 | C.4 |
| 1.690 | B.118 | C.4 |
| 1.691 | B.119 | C.4 |
| 1.692 | B.120 | C.4 |
| 1.693 | B.121 | C.4 |
| 1.694 | B.122 | C.4 |
| 1.695 | B.123 | C.4 |
| 1.696 | B.124 | C.4 |
| 1.697 | B.125 | C.4 |
| 1.698 | B.126 | C.4 |
| 1.699 | B.127 | C.4 |
| 1.700 | B.128 | C.4 |
| 1.701 | B.129 | C.4 |
| 1.702 | B.130 | C.4 |
| 1.703 | B.131 | C.4 |
| 1.704 | B.132 | C.4 |
| 1.705 | B.133 | C.4 |
| 1.706 | B.134 | C.4 |
| 1.707 | B.135 | C.4 |
| 1.708 | B.136 | C.4 |
| 1.709 | B.137 | C.4 |
| 1.710 | B.138 | C.4 |
| 1.711 | B.139 | C.4 |
| 1.712 | B.140 | C.4 |
| 1.713 | B.141 | C.4 |
| 1.714 | B.142 | C.4 |
| 1.715 | B.143 | C.4 |
| 1.716 | B.1 | C.5 |
| 1.717 | B.2 | C.5 |
| 1.718 | B.3 | C.5 |
| 1.719 | B.4 | C.5 |
| 1.720 | B.5 | C.5 |
| 1.721 | B.6 | C.5 |
| 1.722 | B.7 | C.5 |
| 1.723 | B.8 | C.5 |
| 1.724 | B.9 | C.5 |
| 1.725 | B.10 | C.5 |
| 1.726 | B.11 | C.5 |
| 1.727 | B.12 | C.5 |
| 1.728 | B.13 | C.5 |
| 1.729 | B.14 | C.5 |
| 1.730 | B.15 | C.5 |
| 1.731 | B.16 | C.5 |
| 1.732 | B.17 | C.5 |
| 1.733 | B.18 | C.5 |
| 1.734 | B.19 | C.5 |
| 1.735 | B.20 | C.5 |
| 1.736 | B.21 | C.5 |
| 1.737 | B.22 | C.5 |
| 1.738 | B.23 | C.5 |
| 1.739 | B.24 | C.5 |
| 1.740 | B.25 | C.5 |
| 1.741 | B.26 | C.5 |
| 1.742 | B.27 | C.5 |
| 1.743 | B.28 | C.5 |
| 1.744 | B.29 | C.5 |
| 1.745 | B.30 | C.5 |
| 1.746 | B.31 | C.5 |
| 1.747 | B.32 | C.5 |
| 1.748 | B.33 | C.5 |
| 1.749 | B.34 | C.5 |
| 1.750 | B.35 | C.5 |
| 1.751 | B.36 | C.5 |
| 1.752 | B.37 | C.5 |
| 1.753 | B.38 | C.5 |
| 1.754 | B.39 | C.5 |
| 1.755 | B.40 | C.5 |
| 1.756 | B.41 | C.5 |
| 1.757 | B.42 | C.5 |
| 1.758 | B.43 | C.5 |
| 1.759 | B.44 | C.5 |
| 1.760 | B.45 | C.5 |
| 1.761 | B.46 | C.5 |
| 1.762 | B.47 | C.5 |
| 1.763 | B.48 | C.5 |
| 1.764 | B.49 | C.5 |
| 1.765 | B.50 | C.5 |
| 1.766 | B.51 | C.5 |

TABLE 1-continued (compositions 1.1 to 1.1871):

| comp. no. | herbicide B | safener C |
|---|---|---|
| 1.767 | B.52 | C.5 |
| 1.768 | B.53 | C.5 |
| 1.769 | B.54 | C.5 |
| 1.770 | B.55 | C.5 |
| 1.771 | B.56 | C.5 |
| 1.772 | B.57 | C.5 |
| 1.773 | B.58 | C.5 |
| 1.774 | B.59 | C.5 |
| 1.775 | B.60 | C.5 |
| 1.776 | B.61 | C.5 |
| 1.777 | B.62 | C.5 |
| 1.778 | B.63 | C.5 |
| 1.779 | B.64 | C.5 |
| 1.780 | B.65 | C.5 |
| 1.781 | B.66 | C.5 |
| 1.782 | B.67 | C.5 |
| 1.783 | B.68 | C.5 |
| 1.784 | B.69 | C.5 |
| 1.785 | B.70 | C.5 |
| 1.786 | B.71 | C.5 |
| 1.787 | B.72 | C.5 |
| 1.788 | B.73 | C.5 |
| 1.789 | B.74 | C.5 |
| 1.790 | B.75 | C.5 |
| 1.791 | B.76 | C.5 |
| 1.792 | B.77 | C.5 |
| 1.793 | B.78 | C.5 |
| 1.794 | B.79 | C.5 |
| 1.795 | B.80 | C.5 |
| 1.796 | B.81 | C.5 |
| 1.797 | B.82 | C.5 |
| 1.798 | B.83 | C.5 |
| 1.799 | B.84 | C.5 |
| 1.800 | B.85 | C.5 |
| 1.801 | B.86 | C.5 |
| 1.802 | B.87 | C.5 |
| 1.803 | B.88 | C.5 |
| 1.804 | B.89 | C.5 |
| 1.805 | B.90 | C.5 |
| 1.806 | B.91 | C.5 |
| 1.807 | B.92 | C.5 |
| 1.808 | B.93 | C.5 |
| 1.809 | B.94 | C.5 |
| 1.810 | B.95 | C.5 |
| 1.811 | B.96 | C.5 |
| 1.812 | B.97 | C.5 |
| 1.813 | B.98 | C.5 |
| 1.814 | B.99 | C.5 |
| 1.815 | B.100 | C.5 |
| 1.816 | B.101 | C.5 |
| 1.817 | B.102 | C.5 |
| 1.818 | B.103 | C.5 |
| 1.819 | B.104 | C.5 |
| 1.820 | B.105 | C.5 |
| 1.821 | B.106 | C.5 |
| 1.822 | B.107 | C.5 |
| 1.823 | B.108 | C.5 |
| 1.824 | B.109 | C.5 |
| 1.825 | B.110 | C.5 |
| 1.826 | B.111 | C.5 |
| 1.827 | B.112 | C.5 |
| 1.828 | B.113 | C.5 |
| 1.829 | B.114 | C.5 |
| 1.830 | B.115 | C.5 |
| 1.831 | B.116 | C.5 |
| 1.832 | B.117 | C.5 |
| 1.833 | B.118 | C.5 |
| 1.834 | B.119 | C.5 |
| 1.835 | B.120 | C.5 |
| 1.836 | B.121 | C.5 |
| 1.837 | B.122 | C.5 |
| 1.838 | B.123 | C.5 |
| 1.839 | B.124 | C.5 |
| 1.840 | B.125 | C.5 |
| 1.841 | B.126 | C.5 |
| 1.842 | B.127 | C.5 |
| 1.843 | B.128 | C.5 |
| 1.844 | B.129 | C.5 |
| 1.845 | B.130 | C.5 |
| 1.846 | B.131 | C.5 |
| 1.847 | B.132 | C.5 |
| 1.848 | B.133 | C.5 |
| 1.849 | B.134 | C.5 |
| 1.850 | B.135 | C.5 |
| 1.851 | B.136 | C.5 |
| 1.852 | B.137 | C.5 |
| 1.853 | B.138 | C.5 |
| 1.854 | B.139 | C.5 |
| 1.855 | B.140 | C.5 |
| 1.856 | B.141 | C.5 |
| 1.857 | B.142 | C.5 |
| 1.858 | B.143 | C.5 |
| 1.859 | B.1 | C.6 |
| 1.860 | B.2 | C.6 |
| 1.861 | B.3 | C.6 |
| 1.862 | B.4 | C.6 |
| 1.863 | B.5 | C.6 |
| 1.864 | B.6 | C.6 |
| 1.865 | B.7 | C.6 |
| 1.866 | B.8 | C.6 |
| 1.867 | B.9 | C.6 |
| 1.868 | B.10 | C.6 |
| 1.869 | B.11 | C.6 |
| 1.870 | B.12 | C.6 |
| 1.871 | B.13 | C.6 |
| 1.872 | B.14 | C.6 |
| 1.873 | B.15 | C.6 |
| 1.874 | B.16 | C.6 |
| 1.875 | B.17 | C.6 |
| 1.876 | B.18 | C.6 |
| 1.877 | B.19 | C.6 |
| 1.878 | B.20 | C.6 |
| 1.879 | B.21 | C.6 |
| 1.880 | B.22 | C.6 |
| 1.881 | B.23 | C.6 |
| 1.882 | B.24 | C.6 |
| 1.883 | B.25 | C.6 |
| 1.884 | B.26 | C.6 |
| 1.885 | B.27 | C.6 |
| 1.886 | B.28 | C.6 |
| 1.887 | B.29 | C.6 |
| 1.888 | B.30 | C.6 |
| 1.889 | B.31 | C.6 |
| 1.890 | B.32 | C.6 |
| 1.891 | B.33 | C.6 |
| 1.892 | B.34 | C.6 |
| 1.893 | B.35 | C.6 |
| 1.894 | B.36 | C.6 |
| 1.895 | B.37 | C.6 |
| 1.896 | B.38 | C.6 |
| 1.897 | B.39 | C.6 |
| 1.898 | B.40 | C.6 |
| 1.899 | B.41 | C.6 |
| 1.900 | B.42 | C.6 |
| 1.901 | B.43 | C.6 |
| 1.902 | B.44 | C.6 |
| 1.903 | B.45 | C.6 |
| 1.904 | B.46 | C.6 |
| 1.905 | B.47 | C.6 |
| 1.906 | B.48 | C.6 |
| 1.907 | B.49 | C.6 |
| 1.908 | B.50 | C.6 |
| 1.909 | B.51 | C.6 |
| 1.910 | B.52 | C.6 |
| 1.911 | B.53 | C.6 |
| 1.912 | B.54 | C.6 |
| 1.913 | B.55 | C.6 |
| 1.914 | B.56 | C.6 |
| 1.915 | B.57 | C.6 |
| 1.916 | B.58. | C.6 |

TABLE 1-continued (compositions 1.1 to 1.1871):

| comp. no. | herbicide B | safener C |
|---|---|---|
| 1.917 | B.59 | C.6 |
| 1.918 | B.60 | C.6 |
| 1.919 | B.61 | C.6 |
| 1.920 | B.62 | C.6 |
| 1.921 | B.63 | C.6 |
| 1.922 | B.64 | C.6 |
| 1.923 | B.65 | C.6 |
| 1.924 | B.66 | C.6 |
| 1.925 | B.67 | C.6 |
| 1.926 | B.68 | C.6 |
| 1.927 | B.69 | C.6 |
| 1.928 | B.70 | C.6 |
| 1.929 | B.71 | C.6 |
| 1.930 | B.72 | C.6 |
| 1.931 | B.73 | C.6 |
| 1.932 | B.74 | C.6 |
| 1.933 | B.75 | C.6 |
| 1.934 | B.76 | C.6 |
| 1.935 | B.77 | C.6 |
| 1.936 | B.78 | C.6 |
| 1.937 | B.79 | C.6 |
| 1.938 | B.80 | C.6 |
| 1.939 | B.81 | C.6 |
| 1.940 | B.82 | C.6 |
| 1.941 | B.83 | C.6 |
| 1.942 | B.84 | C.6 |
| 1.943 | B.85 | C.6 |
| 1.944 | B.86 | C.6 |
| 1.945 | B.87 | C.6 |
| 1.946 | B.88 | C.6 |
| 1.947 | B.89 | C.6 |
| 1.948 | B.90 | C.6 |
| 1.949 | B.91 | C.6 |
| 1.950 | B.92 | C.6 |
| 1.951 | B.93 | C.6 |
| 1.952 | B.94 | C.6 |
| 1.953 | B.95 | C.6 |
| 1.954 | B.96 | C.6 |
| 1.955 | B.97 | C.6 |
| 1.956 | B.98 | C.6 |
| 1.957 | B.99 | C.6 |
| 1.958 | B.100 | C.6 |
| 1.959 | B.101 | C.6 |
| 1.960 | B.102 | C.6 |
| 1.961 | B.103 | C.6 |
| 1.962 | B.104 | C.6 |
| 1.963 | B.105 | C.6 |
| 1.964 | B.106 | C.6 |
| 1.965 | B.107 | C.6 |
| 1.966 | B.108 | C.6 |
| 1.967 | B.109 | C.6 |
| 1.968 | B.110 | C.6 |
| 1.969 | B.111 | C.6 |
| 1.970 | B.112 | C.6 |
| 1.971 | B.113 | C.6 |
| 1.972 | B.114 | C.6 |
| 1.973 | B.115 | C.6 |
| 1.974 | B.116 | C.6 |
| 1.975 | B.117 | C.6 |
| 1.976 | B.118 | C.6 |
| 1.977 | B.119 | C.6 |
| 1.978 | B.120 | C.6 |
| 1.979 | B.121 | C.6 |
| 1.980 | B.122 | C.6 |
| 1.981 | B.123 | C.6 |
| 1.982 | B.124 | C.6 |
| 1.983 | B.125 | C.6 |
| 1.984 | B.126 | C.6 |
| 1.985 | B.127 | C.6 |
| 1.986 | B.128 | C.6 |
| 1.987 | B.129 | C.6 |
| 1.988 | B.130 | C.6 |
| 1.989 | B.131 | C.6 |
| 1.990 | B.132 | C.6 |
| 1.991 | B.133 | C.6 |
| 1.992 | B.134 | C.6 |
| 1.993 | B.135 | C.6 |
| 1.994 | B.136 | C.6 |
| 1.995 | B.137 | C.6 |
| 1.996 | B.138 | C.6 |
| 1.997 | B.139 | C.6 |
| 1.998 | B.140 | C.6 |
| 1.999 | B.141 | C.6 |
| 1.1000 | B.142 | C.6 |
| 1.1001 | B.143 | C.6 |
| 1.1002 | B.1 | C.7 |
| 1.1003 | B.2 | C.7 |
| 1.1004 | B.3 | C.7 |
| 1.1005 | B.4 | C.7 |
| 1.1006 | B.5 | C.7 |
| 1.1007 | B.6 | C.7 |
| 1.1008 | B.7 | C.7 |
| 1.1009 | B.8 | C.7 |
| 1.1010 | B.9 | C.7 |
| 1.1011 | B.10 | C.7 |
| 1.1012 | B.11 | C.7 |
| 1.1013 | B.12 | C.7 |
| 1.1014 | B.13 | C.7 |
| 1.1015 | B.14 | C.7 |
| 1.1016 | B.15 | C.7 |
| 1.1017 | B.16 | C.7 |
| 1.1018 | B.17 | C.7 |
| 1.1019 | B.18 | C.7 |
| 1.1020 | B.19 | C.7 |
| 1.1021 | B.20 | C.7 |
| 1.1022 | B.21 | C.7 |
| 1.1023 | B.22 | C.7 |
| 1.1024 | B.23 | C.7 |
| 1.1025 | B.24 | C.7 |
| 1.1026 | B.25 | C.7 |
| 1.1027 | B.26 | C.7 |
| 1.1028 | B.27 | C.7 |
| 1.1029 | B.28 | C.7 |
| 1.1030 | B.29 | C.7 |
| 1.1031 | B.30 | C.7 |
| 1.1032 | B.31 | C.7 |
| 1.1033 | B.32 | C.7 |
| 1.1034 | B.33 | C.7 |
| 1.1035 | B.34 | C.7 |
| 1.1036 | B.35 | C.7 |
| 1.1037 | B.36 | C.7 |
| 1.1038 | B.37 | C.7 |
| 1.1039 | B.38 | C.7 |
| 1.1040 | B.39 | C.7 |
| 1.1041 | B.40 | C.7 |
| 1.1042 | B.41 | C.7 |
| 1.1043 | B.42 | C.7 |
| 1.1044 | B.43 | C.7 |
| 1.1045 | B.44 | C.7 |
| 1.1046 | B.45 | C.7 |
| 1.1047 | B.46 | C.7 |
| 1.1048 | B.47 | C.7 |
| 1.1049 | B.48 | C.7 |
| 1.1050 | B.49 | C.7 |
| 1.1051 | B.50 | C.7 |
| 1.1052 | B.51 | C.7 |
| 1.1053 | B.52 | C.7 |
| 1.1054 | B.53 | C.7 |
| 1.1055 | B.54 | C.7 |
| 1.1056 | B.55 | C.7 |
| 1.1057 | B.56 | C.7 |
| 1.1058 | B.57 | C.7 |
| 1.1059 | B.58. | C.7 |
| 1.1060 | B.59 | C.7 |
| 1.1061 | B.60 | C.7 |
| 1.1062 | B.61 | C.7 |
| 1.1063 | B.62 | C.7 |
| 1.1064 | B.63 | C.7 |
| 1.1065 | B.64 | C.7 |
| 1.1066 | B.65 | C.7 |

TABLE 1-continued (compositions 1.1 to 1.1871):

| comp. no. | herbicide B | safener C |
|---|---|---|
| 1.1067 | B.66 | C.7 |
| 1.1068 | B.67 | C.7 |
| 1.1069 | B.68 | C.7 |
| 1.1070 | B.69 | C.7 |
| 1.1071 | B.70 | C.7 |
| 1.1072 | B.71 | C.7 |
| 1.1073 | B.72 | C.7 |
| 1.1074 | B.73 | C.7 |
| 1.1075 | B.74 | C.7 |
| 1.1076 | B.75 | C.7 |
| 1.1077 | B.76 | C.7 |
| 1.1078 | B.77 | C.7 |
| 1.1079 | B.78 | C.7 |
| 1.1080 | B.79 | C.7 |
| 1.1081 | B.80 | C.7 |
| 1.1082 | B.81 | C.7 |
| 1.1083 | B.82 | C.7 |
| 1.1084 | B.83 | C.7 |
| 1.1085 | B.84 | C.7 |
| 1.1086 | B.85 | C.7 |
| 1.1087 | B.86 | C.7 |
| 1.1088 | B.87 | C.7 |
| 1.1089 | B.88 | C.7 |
| 1.1090 | B.89 | C.7 |
| 1.1091 | B.90 | C.7 |
| 1.1092 | B.91 | C.7 |
| 1.1093 | B.92 | C.7 |
| 1.1094 | B.93 | C.7 |
| 1.1095 | B.94 | C.7 |
| 1.1096 | B.95 | C.7 |
| 1.1097 | B.96 | C.7 |
| 1.1098 | B.97 | C.7 |
| 1.1099 | B.98 | C.7 |
| 1.1100 | B.99 | C.7 |
| 1.1101 | B.100 | C.7 |
| 1.1102 | B.101 | C.7 |
| 1.1103 | B.102 | C.7 |
| 1.1104 | B.103 | C.7 |
| 1.1105 | B.104 | C.7 |
| 1.1106 | B.105 | C.7 |
| 1.1107 | B.106 | C.7 |
| 1.1108 | B.107 | C.7 |
| 1.1109 | B.108 | C.7 |
| 1.1110 | B.109 | C.7 |
| 1.1111 | B.110 | C.7 |
| 1.1112 | B.111 | C.7 |
| 1.1113 | B.112 | C.7 |
| 1.1114 | B.113 | C.7 |
| 1.1115 | B.114 | C.7 |
| 1.1116 | B.115 | C.7 |
| 1.1117 | B.116 | C.7 |
| 1.1118 | B.117 | C.7 |
| 1.1119 | B.118 | C.7 |
| 1.1120 | B.119 | C.7 |
| 1.1121 | B.120 | C.7 |
| 1.1122 | B.121 | C.7 |
| 1.1123 | B.122 | C.7 |
| 1.1124 | B.123 | C.7 |
| 1.1125 | B.124 | C.7 |
| 1.1126 | B.125 | C.7 |
| 1.1127 | B.126 | C.7 |
| 1.1128 | B.127 | C.7 |
| 1.1129 | B.128 | C.7 |
| 1.1130 | B.129 | C.7 |
| 1.1131 | B.130 | C.7 |
| 1.1132 | B.131 | C.7 |
| 1.1133 | B.132 | C.7 |
| 1.1134 | B.133 | C.7 |
| 1.1135 | B.134 | C.7 |
| 1.1136 | B.135 | C.7 |
| 1.1137 | B.136 | C.7 |
| 1.1138 | B.137 | C.7 |
| 1.1139 | B.138 | C.7 |
| 1.1140 | B.139 | C.7 |
| 1.1141 | B.140 | C.7 |
| 1.1142 | B.141 | C.7 |
| 1.1143 | B.142 | C.7 |
| 1.1144 | B.143 | C.7 |
| 1.1145 | B.1 | C.8 |
| 1.1146 | B.2 | C.8 |
| 1.1147 | B.3 | C.8 |
| 1.1148 | B.4 | C.8 |
| 1.1149 | B.5 | C.8 |
| 1.1150 | B.6 | C.8 |
| 1.1151 | B.7 | C.8 |
| 1.1152 | B.8 | C.8 |
| 1.1153 | B.9 | C.8 |
| 1.1154 | B.10 | C.8 |
| 1.1155 | B.11 | C.8 |
| 1.1156 | B.12 | C.8 |
| 1.1157 | B.13 | C.8 |
| 1.1158 | B.14 | C.8 |
| 1.1159 | B.15 | C.8 |
| 1.1160 | B.16 | C.8 |
| 1.1161 | B.17 | C.8 |
| 1.1162 | B.18 | C.8 |
| 1.1163 | B.19 | C.8 |
| 1.1164 | B.20 | C.8 |
| 1.1165 | B.21 | C.8 |
| 1.1166 | B.22 | C.8 |
| 1.1167 | B.23 | C.8 |
| 1.1168 | B.24 | C.8 |
| 1.1169 | B.25 | C.8 |
| 1.1170 | B.26 | C.8 |
| 1.1171 | B.27 | C.8 |
| 1.1172 | B.28 | C.8 |
| 1.1173 | B.29 | C.8 |
| 1.1174 | B.30 | C.8 |
| 1.1175 | B.31 | C.8 |
| 1.1176 | B.32 | C.8 |
| 1.1177 | B.33 | C.8 |
| 1.1178 | B.34 | C.8 |
| 1.1179 | B.35 | C.8 |
| 1.1180 | B.36 | C.8 |
| 1.1181 | B.37 | C.8 |
| 1.1182 | B.38 | C.8 |
| 1.1183 | B.39 | C.8 |
| 1.1184 | B.40 | C.8 |
| 1.1185 | B.41 | C.8 |
| 1.1186 | B.42 | C.8 |
| 1.1187 | B.43 | C.8 |
| 1.1188 | B.44 | C.8 |
| 1.1189 | B.45 | C.8 |
| 1.1190 | B.46 | C.8 |
| 1.1191 | B.47 | C.8 |
| 1.1192 | B.48 | C.8 |
| 1.1193 | B.49 | C.8 |
| 1.1194 | B.50 | C.8 |
| 1.1195 | B.51 | C.8 |
| 1.1196 | B.52 | C.8 |
| 1.1197 | B.53 | C.8 |
| 1.1198 | B.54 | C.8 |
| 1.1199 | B.55 | C.8 |
| 1.1200 | B.56 | C.8 |
| 1.1201 | B.57 | C.8 |
| 1.1202 | B.58. | C.8 |
| 1.1203 | B.59 | C.8 |
| 1.1204 | B.60 | C.8 |
| 1.1205 | B.61 | C.8 |
| 1.1206 | B.62 | C.8 |
| 1.1207 | B.63 | C.8 |
| 1.1208 | B.64 | C.8 |
| 1.1209 | B.65 | C.8 |
| 1.1210 | B.66 | C.8 |
| 1.1211 | B.67 | C.8 |
| 1.1212 | B.68 | C.8 |
| 1.1213 | B.69 | C.8 |
| 1.1214 | B.70 | C.8 |
| 1.1215 | B.71 | C.8 |
| 1.1216 | B.72 | C.8 |

TABLE 1-continued (compositions 1.1 to 1.1871):

| comp. no. | herbicide B | safener C |
|---|---|---|
| 1.1217 | B.73 | C.8 |
| 1.1218 | B.74 | C.8 |
| 1.1219 | B.75 | C.8 |
| 1.1220 | B.76 | C.8 |
| 1.1221 | B.77 | C.8 |
| 1.1222 | B.78 | C.8 |
| 1.1223 | B.79 | C.8 |
| 1.1224 | B.80 | C.8 |
| 1.1225 | B.81 | C.8 |
| 1.1226 | B.82 | C.8 |
| 1.1227 | B.83 | C.8 |
| 1.1228 | B.84 | C.8 |
| 1.1229 | B.85 | C.8 |
| 1.1230 | B.86 | C.8 |
| 1.1231 | B.87 | C.8 |
| 1.1232 | B.88 | C.8 |
| 1.1233 | B.89 | C.8 |
| 1.1234 | B.90 | C.8 |
| 1.1235 | B.91 | C.8 |
| 1.1236 | B.92 | C.8 |
| 1.1237 | B.93 | C.8 |
| 1.1238 | B.94 | C.8 |
| 1.1239 | B.95 | C.8 |
| 1.1240 | B.96 | C.8 |
| 1.1241 | B.97 | C.8 |
| 1.1242 | B.98 | C.8 |
| 1.1243 | B.99 | C.8 |
| 1.1244 | B.100 | C.8 |
| 1.1245 | B.101 | C.8 |
| 1.1246 | B.102 | C.8 |
| 1.1247 | B.103 | C.8 |
| 1.1248 | B.104 | C.8 |
| 1.1249 | B.105 | C.8 |
| 1.1250 | B.106 | C.8 |
| 1.1251 | B.107 | C.8 |
| 1.1252 | B.108 | C.8 |
| 1.1253 | B.109 | C.8 |
| 1.1254 | B.110 | C.8 |
| 1.1255 | B.111 | C.8 |
| 1.1256 | B.112 | C.8 |
| 1.1257 | B.113 | C.8 |
| 1.1258 | B.114 | C.8 |
| 1.1259 | B.115 | C.8 |
| 1.1260 | B.116 | C.8 |
| 1.1261 | B.117 | C.8 |
| 1.1262 | B.118 | C.8 |
| 1.1263 | B.119 | C.8 |
| 1.1264 | B.120 | C.8 |
| 1.1265 | B.121 | C.8 |
| 1.1266 | B.122 | C.8 |
| 1.1267 | B.123 | C.8 |
| 1.1268 | B.124 | C.8 |
| 1.1269 | B.125 | C.8 |
| 1.1270 | B.126 | C.8 |
| 1.1271 | B.127 | C.8 |
| 1.1272 | B.128 | C.8 |
| 1.1273 | B.129 | C.8 |
| 1.1274 | B.130 | C.8 |
| 1.1275 | B.131 | C.8 |
| 1.1276 | B.132 | C.8 |
| 1.1277 | B.133 | C.8 |
| 1.1278 | B.134 | C.8 |
| 1.1279 | B.135 | C.8 |
| 1.1280 | B.136 | C.8 |
| 1.1281 | B.137 | C.8 |
| 1.1282 | B.138 | C.8 |
| 1.1283 | B.139 | C.8 |
| 1.1284 | B.140 | C.8 |
| 1.1285 | B.141 | C.8 |
| 1.1286 | B.142 | C.8 |
| 1.1287 | B.143 | C.8 |
| 1.1288 | B.1 | C.9 |
| 1.1289 | B.2 | C.9 |
| 1.1290 | B.3 | C.9 |
| 1.1291 | B.4 | C.9 |
| 1.1292 | B.5 | C.9 |
| 1.1293 | B.6 | C.9 |
| 1.1294 | B.7 | C.9 |
| 1.1295 | B.8 | C.9 |
| 1.1296 | B.9 | C.9 |
| 1.1297 | B.10 | C.9 |
| 1.1298 | B.11 | C.9 |
| 1.1299 | B.12 | C.9 |
| 1.1300 | B.13 | C.9 |
| 1.1301 | B.14 | C.9 |
| 1.1302 | B.15 | C.9 |
| 1.1303 | B.16 | C.9 |
| 1.1304 | B.17 | C.9 |
| 1.1305 | B.18 | C.9 |
| 1.1306 | B.19 | C.9 |
| 1.1307 | B.20 | C.9 |
| 1.1308 | B.21 | C.9 |
| 1.1309 | B.22 | C.9 |
| 1.1310 | B.23 | C.9 |
| 1.1311 | B.24 | C.9 |
| 1.1312 | B.25 | C.9 |
| 1.1313 | B.26 | C.9 |
| 1.1314 | B.27 | C.9 |
| 1.1315 | B.28 | C.9 |
| 1.1316 | B.29 | C.9 |
| 1.1317 | B.30 | C.9 |
| 1.1318 | B.31 | C.9 |
| 1.1319 | B.32 | C.9 |
| 1.1320 | B.33 | C.9 |
| 1.1321 | B.34 | C.9 |
| 1.1322 | B.35 | C.9 |
| 1.1323 | B.36 | C.9 |
| 1.1324 | B.37 | C.9 |
| 1.1325 | B.38 | C.9 |
| 1.1326 | B.39 | C.9 |
| 1.1327 | B.40 | C.9 |
| 1.1328 | B.41 | C.9 |
| 1.1329 | B.42 | C.9 |
| 1.1330 | B.43 | C.9 |
| 1.1331 | B.44 | C.9 |
| 1.1332 | B.45 | C.9 |
| 1.1333 | B.46 | C.9 |
| 1.1334 | B.47 | C.9 |
| 1.1335 | B.48 | C.9 |
| 1.1336 | B.49 | C.9 |
| 1.1337 | B.50 | C.9 |
| 1.1338 | B.51 | C.9 |
| 1.1339 | B.52 | C.9 |
| 1.1340 | B.53 | C.9 |
| 1.1341 | B.54 | C.9 |
| 1.1342 | B.55 | C.9 |
| 1.1343 | B.56 | C.9 |
| 1.1344 | B.57 | C.9 |
| 1.1345 | B.58. | C.9 |
| 1.1346 | B.59 | C.9 |
| 1.1347 | B.60 | C.9 |
| 1.1348 | B.61 | C.9 |
| 1.1349 | B.62 | C.9 |
| 1.1350 | B.63 | C.9 |
| 1.1351 | B.64 | C.9 |
| 1.1352 | B.65 | C.9 |
| 1.1353 | B.66 | C.9 |
| 1.1354 | B.67 | C.9 |
| 1.1355 | B.68 | C.9 |
| 1.1356 | B.69 | C.9 |
| 1.1357 | B.70 | C.9 |
| 1.1358 | B.71 | C.9 |
| 1.1359 | B.72 | C.9 |
| 1.1360 | B.73 | C.9 |
| 1.1361 | B.74 | C.9 |
| 1.1362 | B.75 | C.9 |
| 1.1363 | B.76 | C.9 |
| 1.1364 | B.77 | C.9 |
| 1.1365 | B.78 | C.9 |
| 1.1366 | B.79 | C.9 |

TABLE 1-continued (compositions 1.1 to 1.1871):

| comp. no. | herbicide B | safener C |
|---|---|---|
| 1.1367 | B.80 | C.9 |
| 1.1368 | B.81 | C.9 |
| 1.1369 | B.82 | C.9 |
| 1.1370 | B.83 | C.9 |
| 1.1371 | B.84 | C.9 |
| 1.1372 | B.85 | C.9 |
| 1.1373 | B.86 | C.9 |
| 1.1374 | B.87 | C.9 |
| 1.1375 | B.88 | C.9 |
| 1.1376 | B.89 | C.9 |
| 1.1377 | B.90 | C.9 |
| 1.1378 | B.91 | C.9 |
| 1.1379 | B.92 | C.9 |
| 1.1380 | B.93 | C.9 |
| 1.1381 | B.94 | C.9 |
| 1.1382 | B.95 | C.9 |
| 1.1383 | B.96 | C.9 |
| 1.1384 | B.97 | C.9 |
| 1.1385 | B.98 | C.9 |
| 1.1386 | B.99 | C.9 |
| 1.1387 | B.100 | C.9 |
| 1.1388 | B.101 | C.9 |
| 1.1389 | B.102 | C.9 |
| 1.1390 | B.103 | C.9 |
| 1.1391 | B.104 | C.9 |
| 1.1392 | B.105 | C.9 |
| 1.1393 | B.106 | C.9 |
| 1.1394 | B.107 | C.9 |
| 1.1395 | B.108 | C.9 |
| 1.1396 | B.109 | C.9 |
| 1.1397 | B.110 | C.9 |
| 1.1398 | B.111 | C.9 |
| 1.1399 | B.112 | C.9 |
| 1.1400 | B.113 | C.9 |
| 1.1401 | B.114 | C.9 |
| 1.1402 | B.115 | C.9 |
| 1.1403 | B.116 | C.9 |
| 1.1404 | B.117 | C.9 |
| 1.1405 | B.118 | C.9 |
| 1.1406 | B.119 | C.9 |
| 1.1407 | B.120 | C.9 |
| 1.1408 | B.121 | C.9 |
| 1.1409 | B.122 | C.9 |
| 1.1410 | B.123 | C.9 |
| 1.1411 | B.124 | C.9 |
| 1.1412 | B.125 | C.9 |
| 1.1413 | B.126 | C.9 |
| 1.1414 | B.127 | C.9 |
| 1.1415 | B.128 | C.9 |
| 1.1416 | B.129 | C.9 |
| 1.1417 | B.130 | C.9 |
| 1.1418 | B.131 | C.9 |
| 1.1419 | B.132 | C.9 |
| 1.1420 | B.133 | C.9 |
| 1.1421 | B.134 | C.9 |
| 1.1422 | B.135 | C.9 |
| 1.1423 | B.136 | C.9 |
| 1.1424 | B.137 | C.9 |
| 1.1425 | B.138 | C.9 |
| 1.1426 | B.139 | C.9 |
| 1.1427 | B.140 | C.9 |
| 1.1428 | B.141 | C.9 |
| 1.1429 | B.142 | C.9 |
| 1.1430 | B.143 | C.9 |
| 1.1431 | B.1 | C.10 |
| 1.1432 | B.2 | C.10 |
| 1.1433 | B.3 | C.10 |
| 1.1434 | B.4 | C.10 |
| 1.1435 | B.5 | C.10 |
| 1.1436 | B.6 | C.10 |
| 1.1437 | B.7 | C.10 |
| 1.1438 | B.8 | C.10 |
| 1.1439 | B.9 | C.10 |
| 1.1440 | B.10 | C.10 |
| 1.1441 | B.11 | C.10 |
| 1.1442 | B.12 | C.10 |
| 1.1443 | B.13 | C.10 |
| 1.1444 | B.14 | C.10 |
| 1.1445 | B.15 | C.10 |
| 1.1446 | B.16 | C.10 |
| 1.1447 | B.17 | C.10 |
| 1.1448 | B.18 | C.10 |
| 1.1449 | B.19 | C.10 |
| 1.1450 | B.20 | C.10 |
| 1.1451 | B.21 | C.10 |
| 1.1452 | B.22 | C.10 |
| 1.1453 | B.23 | C.10 |
| 1.1454 | B.24 | C.10 |
| 1.1455 | B.25 | C.10 |
| 1.1456 | B.26 | C.10 |
| 1.1457 | B.27 | C.10 |
| 1.1458 | B.28 | C.10 |
| 1.1459 | B.29 | C.10 |
| 1.1460 | B.30 | C.10 |
| 1.1461 | B.31 | C.10 |
| 1.1462 | B.32 | C.10 |
| 1.1463 | B.33 | C.10 |
| 1.1464 | B.34 | C.10 |
| 1.1465 | B.35 | C.10 |
| 1.1466 | B.36 | C.10 |
| 1.1467 | B.37 | C.10 |
| 1.1468 | B.38 | C.10 |
| 1.1469 | B.39 | C.10 |
| 1.1470 | B.40 | C.10 |
| 1.1471 | B.41 | C.10 |
| 1.1472 | B.42 | C.10 |
| 1.1473 | B.43 | C.10 |
| 1.1474 | B.44 | C.10 |
| 1.1475 | B.45 | C.10 |
| 1.1476 | B.46 | C.10 |
| 1.1477 | B.47 | C.10 |
| 1.1478 | B.48 | C.10 |
| 1.1479 | B.49 | C.10 |
| 1.1480 | B.50 | C.10 |
| 1.1481 | B.51 | C.10 |
| 1.1482 | B.52 | C.10 |
| 1.1483 | B.53 | C.10 |
| 1.1484 | B.54 | C.10 |
| 1.1485 | B.55 | C.10 |
| 1.1486 | B.56 | C.10 |
| 1.1487 | B.57 | C.10 |
| 1.1488 | B.58. | C.10 |
| 1.1489 | B.59 | C.10 |
| 1.1490 | B.60 | C.10 |
| 1.1491 | B.61 | C.10 |
| 1.1492 | B.62 | C.10 |
| 1.1493 | B.63 | C.10 |
| 1.1494 | B.64 | C.10 |
| 1.1495 | B.65 | C.10 |
| 1.1496 | B.66 | C.10 |
| 1.1497 | B.67 | C.10 |
| 1.1498 | B.68 | C.10 |
| 1.1499 | B.69 | C.10 |
| 1.1500 | B.70 | C.10 |
| 1.1501 | B.71 | C.10 |
| 1.1502 | B.72 | C.10 |
| 1.1503 | B.73 | C.10 |
| 1.1504 | B.74 | C.10 |
| 1.1505 | B.75 | C.10 |
| 1.1506 | B.76 | C.10 |
| 1.1507 | B.77 | C.10 |
| 1.1508 | B.78 | C.10 |
| 1.1509 | B.79 | C.10 |
| 1.1510 | B.80 | C.10 |
| 1.1511 | B.81 | C.10 |
| 1.1512 | B.82 | C.10 |
| 1.1513 | B.83 | C.10 |
| 1.1514 | B.84 | C.10 |
| 1.1515 | B.85 | C.10 |
| 1.1516 | B.86 | C.10 |

TABLE 1-continued (compositions 1.1 to 1.1871):

| comp. no. | herbicide B | safener C |
|---|---|---|
| 1.1517 | B.87 | C.10 |
| 1.1518 | B.88 | C.10 |
| 1.1519 | B.89 | C.10 |
| 1.1520 | B.90 | C.10 |
| 1.1521 | B.91 | C.10 |
| 1.1522 | B.92 | C.10 |
| 1.1523 | B.93 | C.10 |
| 1.1524 | B.94 | C.10 |
| 1.1525 | B.95 | C.10 |
| 1.1526 | B.96 | C.10 |
| 1.1527 | B.97 | C.10 |
| 1.1528 | B.98 | C.10 |
| 1.1529 | B.99 | C.10 |
| 1.1530 | B.100 | C.10 |
| 1.1531 | B.101 | C.10 |
| 1.1532 | B.102 | C.10 |
| 1.1533 | B.103 | C.10 |
| 1.1534 | B.104 | C.10 |
| 1.1535 | B.105 | C.10 |
| 1.1536 | B.106 | C.10 |
| 1.1537 | B.107 | C.10 |
| 1.1538 | B.108 | C.10 |
| 1.1539 | B.109 | C.10 |
| 1.1540 | B.110 | C.10 |
| 1.1541 | B.111 | C.10 |
| 1.1542 | B.112 | C.10 |
| 1.1543 | B.113 | C.10 |
| 1.1544 | B.114 | C.10 |
| 1.1545 | B.115 | C.10 |
| 1.1546 | B.116 | C.10 |
| 1.1547 | B.117 | C.10 |
| 1.1548 | B.118 | C.10 |
| 1.1549 | B.119 | C.10 |
| 1.1550 | B.120 | C.10 |
| 1.1551 | B.121 | C.10 |
| 1.1552 | B.122 | C.10 |
| 1.1553 | B.123 | C.10 |
| 1.1554 | B.124 | C.10 |
| 1.1555 | B.125 | C.10 |
| 1.1556 | B.126 | C.10 |
| 1.1557 | B.127 | C.10 |
| 1.1558 | B.128 | C.10 |
| 1.1559 | B.129 | C.10 |
| 1.1560 | B.130 | C.10 |
| 1.1561 | B.131 | C.10 |
| 1.1562 | B.132 | C.10 |
| 1.1563 | B.133 | C.10 |
| 1.1564 | B.134 | C.10 |
| 1.1565 | B.135 | C.10 |
| 1.1566 | B.136 | C.10 |
| 1.1567 | B.137 | C.10 |
| 1.1568 | B.138 | C.10 |
| 1.1569 | B.139 | C.10 |
| 1.1570 | B.140 | C.10 |
| 1.1571 | B.141 | C.10 |
| 1.1572 | B.142 | C.10 |
| 1.1573 | B.143 | C.10 |
| 1.1574 | B.1 | C.11 |
| 1.1575 | B.2 | C.11 |
| 1.1576 | B.3 | C.11 |
| 1.1577 | B.4 | C.11 |
| 1.1578 | B.5 | C.11 |
| 1.1579 | B.6 | C.11 |
| 1.1580 | B.7 | C.11 |
| 1.1581 | B.8 | C.11 |
| 1.1582 | B.9 | C.11 |
| 1.1583 | B.10 | C.11 |
| 1.1584 | B.11 | C.11 |
| 1.1585 | B.12 | C.11 |
| 1.1586 | B.13 | C.11 |
| 1.1587 | B.14 | C.11 |
| 1.1588 | B.15 | C.11 |
| 1.1589 | B.16 | C.11 |
| 1.1590 | B.17 | C.11 |
| 1.1591 | B.18 | C.11 |
| 1.1592 | B.19 | C.11 |
| 1.1593 | B.20 | C.11 |
| 1.1594 | B.21 | C.11 |
| 1.1595 | B.22 | C.11 |
| 1.1596 | B.23 | C.11 |
| 1.1597 | B.24 | C.11 |
| 1.1598 | B.25 | C.11 |
| 1.1599 | B.26 | C.11 |
| 1.1600 | B.27 | C.11 |
| 1.1601 | B.28 | C.11 |
| 1.1602 | B.29 | C.11 |
| 1.1603 | B.30 | C.11 |
| 1.1604 | B.31 | C.11 |
| 1.1605 | B.32 | C.11 |
| 1.1606 | B.33 | C.11 |
| 1.1607 | B.34 | C.11 |
| 1.1608 | B.35 | C.11 |
| 1.1609 | B.36 | C.11 |
| 1.1610 | B.37 | C.11 |
| 1.1611 | B.38 | C.11 |
| 1.1612 | B.39 | C.11 |
| 1.1613 | B.40 | C.11 |
| 1.1614 | B.41 | C.11 |
| 1.1615 | B.42 | C.11 |
| 1.1616 | B.43 | C.11 |
| 1.1617 | B.44 | C.11 |
| 1.1618 | B.45 | C.11 |
| 1.1619 | B.46 | C.11 |
| 1.1620 | B.47 | C.11 |
| 1.1621 | B.48 | C.11 |
| 1.1622 | B.49 | C.11 |
| 1.1623 | B.50 | C.11 |
| 1.1624 | B.51 | C.11 |
| 1.1625 | B.52 | C.11 |
| 1.1626 | B.53 | C.11 |
| 1.1627 | B.54 | C.11 |
| 1.1628 | B.55 | C.11 |
| 1.1629 | B.56 | C.11 |
| 1.1630 | B.57 | C.11 |
| 1.1631 | B.58. | C.11 |
| 1.1632 | B.59 | C.11 |
| 1.1633 | B.60 | C.11 |
| 1.1634 | B.61 | C.11 |
| 1.1635 | B.62 | C.11 |
| 1.1636 | B.63 | C.11 |
| 1.1637 | B.64 | C.11 |
| 1.1638 | B.65 | C.11 |
| 1.1639 | B.66 | C.11 |
| 1.1640 | B.67 | C.11 |
| 1.1641 | B.68 | C.11 |
| 1.1642 | B.69 | C.11 |
| 1.1643 | B.70 | C.11 |
| 1.1644 | B.71 | C.11 |
| 1.1645 | B.72 | C.11 |
| 1.1646 | B.73 | C.11 |
| 1.1647 | B.74 | C.11 |
| 1.1648 | B.75 | C.11 |
| 1.1649 | B.76 | C.11 |
| 1.1650 | B.77 | C.11 |
| 1.1651 | B.78 | C.11 |
| 1.1652 | B.79 | C.11 |
| 1.1653 | B.80 | C.11 |
| 1.1654 | B.81 | C.11 |
| 1.1655 | B.82 | C.11 |
| 1.1656 | B.83 | C.11 |
| 1.1657 | B.84 | C.11 |
| 1.1658 | B.85 | C.11 |
| 1.1659 | B.86 | C.11 |
| 1.1660 | B.87 | C.11 |
| 1.1661 | B.88 | C.11 |
| 1.1662 | B.89 | C.11 |
| 1.1663 | B.90 | C.11 |
| 1.1664 | B.91 | C.11 |
| 1.1665 | B.92 | C.11 |
| 1.1666 | B.93 | C.11 |

TABLE 1-continued (compositions 1.1 to 1.1871):

| comp. no. | herbicide B | safener C |
|---|---|---|
| 1.1667 | B.94 | C.11 |
| 1.1668 | B.95 | C.11 |
| 1.1669 | B.96 | C.11 |
| 1.1670 | B.97 | C.11 |
| 1.1671 | B.98 | C.11 |
| 1.1672 | B.99 | C.11 |
| 1.1673 | B.100 | C.11 |
| 1.1674 | B.101 | C.11 |
| 1.1675 | B.102 | C.11 |
| 1.1676 | B.103 | C.11 |
| 1.1677 | B.104 | C.11 |
| 1.1678 | B.105 | C.11 |
| 1.1679 | B.106 | C.11 |
| 1.1680 | B.107 | C.11 |
| 1.1681 | B.108 | C.11 |
| 1.1682 | B.109 | C.11 |
| 1.1683 | B.110 | C.11 |
| 1.1684 | B.111 | C.11 |
| 1.1685 | B.112 | C.11 |
| 1.1686 | B.113 | C.11 |
| 1.1687 | B.114 | C.11 |
| 1.1688 | B.115 | C.11 |
| 1.1689 | B.116 | C.11 |
| 1.1690 | B.117 | C.11 |
| 1.1691 | B.118 | C.11 |
| 1.1692 | B.119 | C.11 |
| 1.1693 | B.120 | C.11 |
| 1.1694 | B.121 | C.11 |
| 1.1695 | B.122 | C.11 |
| 1.1696 | B.123 | C.11 |
| 1.1697 | B.124 | C.11 |
| 1.1698 | B.125 | C.11 |
| 1.1699 | B.126 | C.11 |
| 1.1700 | B.127 | C.11 |
| 1.1701 | B.128 | C.11 |
| 1.1702 | B.129 | C.11 |
| 1.1703 | B.130 | C.11 |
| 1.1704 | B.131 | C.11 |
| 1.1705 | B.132 | C.11 |
| 1.1706 | B.133 | C.11 |
| 1.1707 | B.134 | C.11 |
| 1.1708 | B.135 | C.11 |
| 1.1709 | B.136 | C.11 |
| 1.1710 | B.137 | C.11 |
| 1.1711 | B.138 | C.11 |
| 1.1712 | B.139 | C.11 |
| 1.1713 | B.140 | C.11 |
| 1.1714 | B.141 | C.11 |
| 1.1715 | B.142 | C.11 |
| 1.1716 | B.143 | C.11 |
| 1.1717 | B.1 | C.12 |
| 1.1718 | B.2 | C.12 |
| 1.1719 | B.3 | C.12 |
| 1.1720 | B.4 | C.12 |
| 1.1721 | B.5 | C.12 |
| 1.1722 | B.6 | C.12 |
| 1.1723 | B.7 | C.12 |
| 1.1724 | B.8 | C.12 |
| 1.1725 | B.9 | C.12 |
| 1.1726 | B.10 | C.12 |
| 1.1727 | B.11 | C.12 |
| 1.1728 | B.12 | C.12 |
| 1.1729 | B.13 | C.12 |
| 1.1730 | B.14 | C.12 |
| 1.1731 | B.15 | C.12 |
| 1.1732 | B.16 | C.12 |
| 1.1733 | B.17 | C.12 |
| 1.1734 | B.18 | C.12 |
| 1.1735 | B.19 | C.12 |
| 1.1736 | B.20 | C.12 |
| 1.1737 | B.21 | C.12 |
| 1.1738 | B.22 | C.12 |
| 1.1739 | B.23 | C.12 |
| 1.1740 | B.24 | C.12 |
| 1.1741 | B.25 | C.12 |
| 1.1742 | B.26 | C.12 |
| 1.1743 | B.27 | C.12 |
| 1.1744 | B.28 | C.12 |
| 1.1745 | B.29 | C.12 |
| 1.1746 | B.30 | C.12 |
| 1.1747 | B.31 | C.12 |
| 1.1748 | B.32 | C.12 |
| 1.1749 | B.33 | C.12 |
| 1.1750 | B.34 | C.12 |
| 1.1751 | B.35 | C.12 |
| 1.1752 | B.36 | C.12 |
| 1.1753 | B.37 | C.12 |
| 1.1754 | B.38 | C.12 |
| 1.1755 | B.39 | C.12 |
| 1.1756 | B.40 | C.12 |
| 1.1757 | B.41 | C.12 |
| 1.1758 | B.42 | C.12 |
| 1.1759 | B.43 | C.12 |
| 1.1760 | B.44 | C.12 |
| 1.1761 | B.45 | C.12 |
| 1.1762 | B.46 | C.12 |
| 1.1763 | B.47 | C.12 |
| 1.1764 | B.48 | C.12 |
| 1.1765 | B.49 | C.12 |
| 1.1766 | B.50 | C.12 |
| 1.1767 | B.51 | C.12 |
| 1.1768 | B.52 | C.12 |
| 1.1769 | B.53 | C.12 |
| 1.1770 | B.54 | C.12 |
| 1.1771 | B.55 | C.12 |
| 1.1772 | B.56 | C.12 |
| 1.1773 | B.57 | C.12 |
| 1.1774 | B.58. | C.12 |
| 1.1775 | B.59 | C.12 |
| 1.1776 | B.60 | C.12 |
| 1.1777 | B.61 | C.12 |
| 1.1778 | B.62 | C.12 |
| 1.1779 | B.63 | C.12 |
| 1.1780 | B.64 | C.12 |
| 1.1781 | B.65 | C.12 |
| 1.1782 | B.66 | C.12 |
| 1.1783 | B.67 | C.12 |
| 1.1784 | B.68 | C.12 |
| 1.1785 | B.69 | C.12 |
| 1.1786 | B.70 | C.12 |
| 1.1787 | B.71 | C.12 |
| 1.1788 | B.72 | C.12 |
| 1.1789 | B.73 | C.12 |
| 1.1790 | B.74 | C.12 |
| 1.1791 | B.75 | C.12 |
| 1.1792 | B.76 | C.12 |
| 1.1793 | B.77 | C.12 |
| 1.1794 | B.78 | C.12 |
| 1.1795 | B.79 | C.12 |
| 1.1796 | B.80 | C.12 |
| 1.1797 | B.81 | C.12 |
| 1.1798 | B.82 | C.12 |
| 1.1799 | B.83 | C.12 |
| 1.1800 | B.84 | C.12 |
| 1.1801 | B.85 | C.12 |
| 1.1802 | B.86 | C.12 |
| 1.1803 | B.87 | C.12 |
| 1.1804 | B.88 | C.12 |
| 1.1805 | B.89 | C.12 |
| 1.1806 | B.90 | C.12 |
| 1.1807 | B.91 | C.12 |
| 1.1808 | B.92 | C.12 |
| 1.1809 | B.93 | C.12 |
| 1.1810 | B.94 | C.12 |
| 1.1811 | B.95 | C.12 |
| 1.1812 | B.96 | C.12 |
| 1.1813 | B.97 | C.12 |
| 1.1814 | B.98 | C.12 |
| 1.1815 | B.99 | C.12 |
| 1.1816 | B.100 | C.12 |

TABLE 1-continued (compositions 1.1 to 1.1871):

| comp. no. | herbicide B | safener C |
|---|---|---|
| 1.1817 | B.101 | C.12 |
| 1.1818 | B.102 | C.12 |
| 1.1819 | B.103 | C.12 |
| 1.1820 | B.104 | C.12 |
| 1.1821 | B.105 | C.12 |
| 1.1822 | B.106 | C.12 |
| 1.1823 | B.107 | C.12 |
| 1.1824 | B.108 | C.12 |
| 1.1825 | B.109 | C.12 |
| 1.1826 | B.110 | C.12 |
| 1.1827 | B.111 | C.12 |
| 1.1828 | B.112 | C.12 |
| 1.1829 | B.113 | C.12 |
| 1.1830 | B.114 | C.12 |
| 1.1831 | B.115 | C.12 |
| 1.1832 | B.116 | C.12 |
| 1.1833 | B.117 | C.12 |
| 1.1834 | B.118 | C.12 |
| 1.1835 | B.119 | C.12 |
| 1.1836 | B.120 | C.12 |
| 1.1837 | B.121 | C.12 |
| 1.1838 | B.122 | C.12 |
| 1.1839 | B.123 | C.12 |
| 1.1840 | B.124 | C.12 |
| 1.1841 | B.125 | C.12 |
| 1.1842 | B.126 | C.12 |
| 1.1843 | B.127 | C.12 |
| 1.1844 | B.128 | C.12 |
| 1.1845 | B.129 | C.12 |
| 1.1846 | B.130 | C.12 |
| 1.1847 | B.131 | C.12 |
| 1.1848 | B.132 | C.12 |
| 1.1849 | B.133 | C.12 |
| 1.1850 | B.134 | C.12 |
| 1.1851 | B.135 | C.12 |
| 1.1852 | B.136 | C.12 |
| 1.1853 | B.137 | C.12 |
| 1.1854 | B.138 | C.12 |
| 1.1855 | B.139 | C.12 |
| 1.1856 | B.140 | C.12 |
| 1.1857 | B.141 | C.12 |
| 1.1858 | B.142 | C.12 |
| 1.1859 | B.143 | C.12 |
| 1.1860 | — | C.1 |
| 1.1861 | — | C.2 |
| 1.1862 | — | C.3 |
| 1.1863 | — | C.4 |
| 1.1864 | — | C.5 |
| 1.1865 | — | C.6 |
| 1.1866 | — | C.7 |
| 1.1867 | — | C.8 |
| 1.1868 | — | C.9 |
| 1.1869 | — | C.10 |
| 1.1870 | — | C.11 |
| 1.1871 | — | C.12 |

The specific number for each single composition is deductible as follows:

Composition 1.777 for example comprises the uracil Ia48, metamitron (B.62) and fenchlorazole (C.5) (see table 1, entry 1.777; as well as table B, entry B.62 and table C, entry C.5).

Composition 2.777 for example comprises the uracil Ib48, metamitron (B.62) and fenchlorazole (C.5) (see the definition for compositions 2.1 to 2.1871 below as well as table 1, entry 1.777; table B, entry B.62 and table C, entry C.5).

Composition 7.777 for example comprises imazapic (B30), and the uracil Ia48, metamitron (B.62) and fenchlorazole (C.5) (see the definition for compositions 7.1 to 7.1871 below as well as table 1, entry 1.777; table B, entry B.62 and table C, entry C.5).

Also especially preferred are compositions 2.1. to 2.1871 which differ from the corresponding compositions 1.1 to 1.1871 only in that they comprise as the active compound A the uracil Ib48.

Also especially preferred are compositions 3.1. to 3.1871 which differ from the corresponding compositions 1.1 to 1.1871 only in that they comprise as the active cornpound A the uracil Ic48.

Also especially preferred are compositions 4.1. to 4.1871 which differ from the corresponding compositions 1.1 to 1.1871 only in that they additionally comprise B.2 as further herbicide B.

Also especially preferred are compositions 5.1. to 5.1871 which differ from the corresponding compositions 1.1 to 1.1871 only in that they additionally comprise B.7 as further herbicide B.

Also especially preferred are compositions 6.1. to 6.1871 which differ from the corresponding compositions 1.1 to 1.1871 only in that they additionally comprise B.29 as further herbicide B.

Also especially preferred are compositions 7.1. to 7.1871 which differ from the corresponding compositions 1.1 to 1.1871 only in that they additionally comprise B.30 as further herbicide B.

Also especially preferred are compositions 8.1. to 8.1871 which differ from the corresponding compositions 1.1 to 1.1871 only in that they additionally comprise B.31 as further herbicide B.

Also especially preferred are compositions 9.1. to 9.1871 which differ from the corresponding compositions 1.1 to 1.1871 only in that they additionally comprise B.32 as further herbicide B.

Also especially preferred are compositions 10.1. to 10.1871 which differ from the corresponding compositions 1.1 to 1.1871 only in that they additionally comprise B.33 as further herbicide B.

Also especially preferred are compositions 11.1. to 11.1871 which differ from the corresponding compositions 1.1 to 1.1871 only in, that they additionally comprise B.40 as further herbicide B.

Also especially preferred are compositions 12.1. to 12.1871 which differ from the corresponding compositions 1.1 to 1.1871 only in that they additionally comprise B.44 as further herbicide B.

Also especially preferred are compositions 13.1. to 13.1871 which differ from the corresponding compositions 1.1 to 1.1871 only in that they additionally comprise B.45 as further herbicide B.

Also especially preferred are compositions 14.1. to 14.1871 which differ from the corresponding compositions 1.1 to 1.1871 only in that they additionally comprise B.52 as further herbicide B.

Also especially preferred are compositions 15.1. to 15.1871 which differ from the corresponding compositions 1.1 to 1.1871 only in that they additionally comprise B.53 as further herbicide B.

Also especially preferred are compositions 16.1. to 16.1871 which differ from the corresponding compositions 1.1 to 1.1871 only in that they additionally comprise B.54 as further herbicide B.

Also especially preferred are compositions 17.1. to 17.1871 which differ from the corresponding compositions 1.1 to 1.1871 only in that they additionally comprise B.55 as further herbicide B.

Also especially preferred are compositions 18.1. to 18.1871 which differ from the corresponding compositions 1.1 to 1.1871 only in that they additionally comprise B.56 as further herbicide B.

Also especially preferred are compositions 19.1. to 19.1871 which differ from the corresponding compositions 1.1 to 1.1871 only in that they additionally comprise B.57 as further herbicide B.

Also especially preferred are compositions 20.1. to 20.1871 which differ from the corresponding compositions 1.1 to 1.1871 only in that they additionally comprise B.60 as further herbicide B.

Also especially preferred are compositions 21.1. to 21.1871 which differ from the corresponding compositions 1.1 to 1.1871 only in that they additionally comprise B.65 as further herbicide B.

Also especially preferred are compositions 22.1. to 22.1871 which differ from the corresponding compositions 1.1 to 1.1871 only in that they additionally comprise B.66 as further herbicide B.

Also especially preferred are compositions 23.1. to 23.1871 which differ from the corresponding compositions 1.1 to 1.1871 only in that they additionally comprise B.69 as further herbicide B.

Also especially preferred are compositions 24.1. to 24.1871 which differ from the corresponding compositions 1.1 to 1.1871 only in that they additionally comprise B.72 as further herbicide B.

Also especially preferred are compositions 25.1. to 25.1871 which differ from the corresponding compositions 1.1 to 1.1871 only in that they additionally comprise B.73 as further herbicide B.

Also especially preferred are compositions 26.1. to 26.1871 which differ from the corresponding compositions 1.1 to 1.1871 only in that they additionally comprise B.76 as further herbicide B.

Also especially preferred are compositions 27.1. to 27.1871 which differ from the corresponding compositions 1.1 to 1.1871 only in that they additionally comprise B.77 as further herbicide B.

Also especially preferred are compositions 28.1. to 28.1871 which differ from the corresponding compositions 1.1 to 1.1871 only in that they additionally comprise B.82 as further herbicide B.

Also especially preferred are compositions 29.1. to 29.1871 which differ from the corresponding compositions 1.1 to 1.1871 only in that they additionally comprise B.83 as further herbicide B.

Also especially preferred are compositions 30.1. to 30.1871 which differ from the corresponding compositions 1.1 to 1.1871 only in that they additionally comprise B.86 as further herbicide B.

Also especially preferred are compositions 31.1. to 31.1871 which differ from the corresponding compositions 1.1 to 1.1871 only in that they additionally comprise B.86 and B.54 as further herbicides B.

Also especially preferred are compositions 32.1. to 32.1871 which differ from the corresponding compositions 1.1 to 1.1871 only in that they additionally comprise B.86 and B.60 as further herbicides B.

Also especially preferred are compositions 33.1. to 33.1871 which differ from the corresponding compositions 1.1 to 1.1871 only in that they additionally comprise B.86 and B.66 as further herbicides B.

Also especially preferred are compositions 34.1. to 34.1871 which differ from the corresponding compositions 1.1 to 1.1871 only in that they additionally comprise B. 87 as further herbicide B.

Also especially preferred are compositions 35.1. to 35.1871 which differ from the corresponding compositions 1.1 to 1.1871 only in, that they additionally comprise B. 87 and B.54 as further herbicides B.

Also especially preferred are compositions 36.1. to 36.1871 which differ from the corresponding compositions 1.1 to 1.1871 only in that they additionally comprise B. 87 and B.60 as further herbicides B.

Also especially preferred are compositions 37.1. to 37.1871 which differ from the corresponding, compositions 1.1 to 1.1871 only in that they additionally comprise B. 87 and B.66 as further herbicides B.

Also especially preferred are compositions 38.1. to 38.1871 which differ from the corresponding, compositions 1.1 to 1.1871 only in that they additionally comprise B.89 as further herbicide B.

Also especially preferred are compositions 39.1. to 39.1871 which differ from the corresponding compositions 1.1 to 1.1871 only in that they additionally comprise B. 90 as further herbicide B.

Also especially preferred are compositions 40.1. to 40.1871 which differ from the corresponding compositions 1.1 to 1.1871 only in that they additionally comprise B. 90 and B.54 as further herbicides B.

Also especially preferred are compositions 41.1. to 41.1871 which differ from the corresponding compositions 1.1 to 1.1871 only in that they additionally comprise B. 90 and B.601 as further herbicides B.

Also especially preferred are compositions 42.1. to 42.1871 which differ from the corresponding compositions 1.1 to 1.1871 only in that they additionally comprise B. 90 and B.66 as further herbicides B.

Also especially preferred are compositions 43.1. to 43.1871 which differ from the corresponding compositions 1.1 to 1.1871 only in that they additionally comprise B.92 as further herbicide B.

Also especially preferred are compositions 44.1. to 44.1871 which differ from the corresponding compositions 1.1 to 1.1871 only in that they additionally comprise B.93 as further herbicide B.

Also especially preferred are compositions 45.1. to 45.1871 which differ from the corresponding compositions 1.1 to 1.1871 only in that they additionally comprise B.93 and B.54 as further herbicides B.

Also especially preferred are compositions 46.1. to 46.1871 which differ from the corresponding compositions 1.1 to 1.1871 only in that they additionally comprise B.93 and B.60 as further herbicides B.

Also especially preferred are compositions 47.1. to 47.1871 which differ from the corresponding compositions 1.1 to 1.1871 only in that they additionally comprise B.93 and B.66 as further herbicides B.

Also especially preferred are compositions 48.1. to 48.1871 which differ from the corresponding compositions 1.1 to 1.1871 only in that they additionally comprise B.97 as further herbicide B.

Also especially preferred are compositions 49.1. to 49.1871 which differ from the corresponding compositions 1.1 to 1.1871 only in that they additionally comprise B.97 and B.54 as further herbicides B.

Also especially preferred are compositions 50.1. to 50.1871 which differ from the corresponding compositions 1.1 to 1.1871 only in that they additionally comprise B.97 and B.76 as further herbicides B.

Also especially preferred are compositions 51.1. to 51.1871 which differ from the corresponding compositions 1.1 to 1.1871 only in that they additionally comprise B.97 and B.86 as further herbicides B.
Also especially preferred are compositions 52.1. to 52.1871 which differ from the corresponding compositions 1.1 to 1.1871 only in that they additionally comprise B.97 and B.87 as further herbicides B.
Also especially preferred are compositions 53.1. to 53.1871 which differ from the corresponding compositions 1.1 to 1.1871 only in that they additionally comprise B.97 and B.90 as further herbicides B.
Also especially preferred are compositions 54.1. to 54.1871 which differ from the corresponding compositions 1.1 to 1.1871 only in that they additionally comprise B.97 and B.93 as further herbicides B.
Also especially preferred are compositions 55.1. to 55.1871 which differ from the corresponding compositions 1.1 to 1.1871 only in that they additionally comprise B.97 and B.105 as further herbicides B.
Also especially preferred are compositions 56.1. to 56.1871 which differ from the corresponding compositions 1.1 to 1.1871 only in that they additionally comprise B.100 as further herbicide B.
Also especially preferred are compositions 57.1. to 57.1871 which differ from the corresponding compositions 1.1 to 1.1871 only in that they additionally comprise B.103 as further herbicide B.
Also especially preferred are compositions 58.1. to 58.1871 which differ from the corresponding compositions 1.1 to 1.1871 only in that they additionally comprise B.105 as further herbicide B.
Also especially preferred are compositions 59.1. to 59.1871 which differ from the corresponding compositions 1.1 to 1.1871 only in that they additionally comprise B.108 as further herbicide B.
Also especially preferred are compositions 60.1. to 60.1871 which differ from the corresponding compositions 1.1 to 1.1871 only in that they additionally comprise B.109 as further herbicide B.
Also especially preferred are compositions 61.1. to 61.1871 which differ from the corresponding compositions 1.1 to 1.1871 only in that they additionally comprise B.110 as further herbicide B.
Also especially preferred are compositions 62.1. to 62.1871 which differ from the corresponding compositions 1.1 to 1.1871 only in that they additionally comprise B.112 as further herbicide B.
Also especially preferred are compositions 63.1. to 63.1871 which differ from the corresponding compositions 1.1 to 1.1871 only in that they additionally comprise 8.114 as further herbicide B.
Also especially preferred are compositions 64.1. to 64.1871 which differ from the corresponding compositions 11.1 to 1.1871 only in that they additionally comprise 8.115 as further herbicide B.
Also especially preferred are compositions 65.1. to 65.1871 which differ from the corresponding compositions 1.1 to 1.1871 only in that they additionally comprise B.119 as further herbicide B.
Also especially preferred are compositions 66.1. to 66.1871 which differ from the corresponding compositions 1.1 to 1.1871 only in that they additionally comprise B.121 as further herbicide B.
Also especially preferred are compositions 67.1. to 67.1871 which differ from the corresponding compositions 1.1 to 1.1871 only in that they additionally comprise B.122 as further herbicide B.
Also especially preferred are compositions 68.1. to 68.1871 which differ from the corresponding compositions 1.1 to 1.1871 only in that they additionally comprise B.124 as further herbicide B.
Also especially preferred are compositions 69.1. to 69.1871 which differ from the corresponding compositions 1.1 to 1.1871 only in that they additionally comprise B.125 as further herbicide B.
Also especially preferred are compositions 70.1. to 70.1871 which differ from the corresponding compositions 1.1 to 1.1871 only in that they additionally comprise B.132 as further herbicide B.

EXAMPLES

Hereinbelow, the preparation of the uracils of the formula I is illustrated by examples; however, the subject matter of the present invention is not limited to the examples given.

Example 1

1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (compound Ia48)

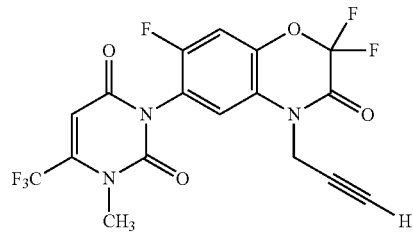 [SMILES: C#CCN1C(=O)C(F)(F)Oc2cc(F)c(-n3c(=O)cc(C(F)(F)F)n(C)c3=O)cc21]

1.2: 2-amino-5-fluorophenol

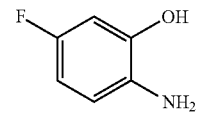

To 5-fluoro-2-nitrophenol (26.63 g, 170 mmol) in ethanol under $N_2$ atmosphere was added palladium on carbon (10 wt %, 250 mg, 0.235 mmol). The mixture was flushed with $H_2$ and stirred at RT under $H_2$ (balloon) until complete conversion according to thin layer chromatography (TLC) analysis. Pd/C was removed by filtration and the filtrate was concentrated to yield 21.6 g of the title compound.
$^1$H NMR (DMSO): 4.5 (br, 2H), 6.35 (dd, 1H), 6.45 (dd, 1H), 6.50 (dd, 1H), 9.5 (br, 1H).

1.2: 2-bromo-2,2-difluoro-N-(4-fluoro-2-hydroxyphenyl)acetamide

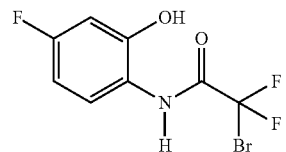 [SMILES: O=C(Nc1ccc(F)cc1O)C(F)(F)Br]

Alternative a)

To 2-amino-5-fluorophenol (14 g, 110 mmol) in dry tetrahydrofuran at 0° C. was added sodium hydride (55 wt % in mineral oil; 4.81 g, 110 mmol). The resulting mixture was stirred for 15 minutes at −15° C. Subsequently ethyl 2-bromo-2,2-difluoroacetate (24.59 g, 121 mmol) was added dropwise and the resulting mixture was stirred at 0° C. for two hours. The reaction mixture was quenched with saturated aqueous NH$_4$Cl solution and extracted with ethyl acetate. The combined extracts were washed with brine, dried with Na$_2$SO$_4$ and concentrated to yield 33 g of the title compound.

$^1$H NMR (DMSO): 3.3 (br, 1H), 6.8 (m, 2H), 7.25 (dd, 1H), 10.4 (br, 1H).

Alternative b)

To 2-amino-5-fluorophenol (200 mg, 1.573 mmol) in dry tetrahydrofuran at 0° C. was added sodium hydride (55 wt % in mineral oil, 68.6 mg, 1.573 mmol). The resulting mixture was stirred for 15 minutes at −15° C. Subsequently methyl 2-bromo-2,2-difluoroacetate (327 mg, 1.731 mmol) was added dropwise and the resulting mixture was stirred at 0° C. for two hours. The reaction mixture was quenched in saturated aqueous NH$_4$Cl solution and extracted with ethyl acetate. The combined extracts were washed with brine, dried with Na$_2$SO$_4$ and concentrated to yield 450 mg of the title compound $^1$H NMR (DMSO): 3.3 (br, 1H), 6.8 (m, 2H), 7.25 (dd, 1H), 10.4 (br, 1H).

1.3:
2,2,7-trifluoro-2H-benzo[b][1,4]oxazin-3(4H)-one

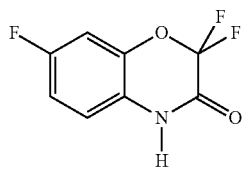

To 2-bromo-2,2-difluoro-N-(4-fluoro-2-hydroxyphenyl)acetamide (33 g, 116 mmol) in dry toluene was added 1,8-diazabicyclo[5.4.0]undec-7-en (DBU, 17.51 ml, 116 mmol). The resulting mixture was stirred overnight at 80° C. The reaction was quenched in saturated aqueous NH$_4$Cl solution and extracted with ethyl acetate. The combined extracts were washed with brine, dried with Na$_2$SO$_4$ and concentrated to afford 24.94 g of the title compound.

GCMS m/e (M+)=203

1.4: 2,2,7-trifluoro-6-nitro-2H-benzo[b][1,4]oxazin-3(4H)-one

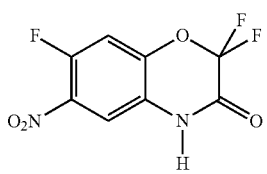 [SMILES: O=C1Nc2cc([N+](=O)[O-])c(F)cc2OC1(F)F]

2,2,7-trifluoro-2H-benzo[b][1,4]oxazin-3(4H)-one (2.5 g, 12.31 mmol) was dissolved in sulfuric acid (40 ml, 750 mmol). The reaction mixture was cooled to 0-5° C. Slowly nitric acid (1.761 ml, 39.7 mmol) was added dropwise and the temperature was maintained between 0-5° C. The reaction mixture was stirred for 30 min at this temperature. Then the reaction mixture was added dropwise to vigorously stirred cold water. A solid was formed, which was extracted with dichloromethane. The combined extracts were dried over Na$_2$SO$_4$, and concentrated to yield 2.56 g of the title compound as a brown solid.

GC/MS m/e (M+)=248

$^1$H-NMR (CDCl$_3$): 2.90 (br, 1H), 7.15 (d, 1H), 7.80 (d, 1H).

1.5: 2,2,7-trifluoro-6-nitro-4-(prop-2-ynyl)-2Hbenzo[b][1,4]oxazin-3(4H)-one

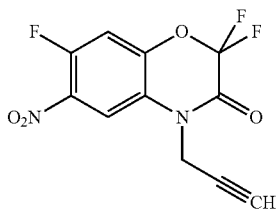

To 2,2,7-trifluoro-6-nitro-2H-benzo[b][1,4]oxazin-3(4H)-one (6.9 g, 27.8 mmol) and potassium carbonate (4.61 g, 33.4 mmol) in dry N,N-dimethylformamide at RT was dropwise added 3-bromoprop-1-yne (80 wt % in toluene; 4.96 g, 33.4 mmol). The resulting mixture was stirred at RT overnight. The reaction mixture was poured in saturated aqueous NH$_4$Cl solution and extracted with ethyl acetate. The combined extracts were washed with aqueous NaCl solution, dried with Na$_2$SO$_4$, concentrated and chased with toluene to yield 7.06 g of the title compound as dark brown solid.

GCMS m/e (M+)=286

1.6: 6-amino-2,2,7-trifluoro-4-(prop-2-ynyl)-2Hbenzo[b][1,4]oxazin-3(4H)-one

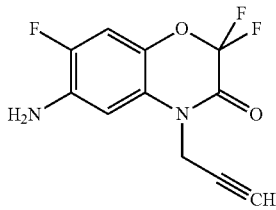 [SMILES: C#CCN1C(=O)C(F)(F)Oc2cc(F)c([N+](=O)[O-])cc21]

To ammonium chloride (3.96 g, 74.0 mmol) in water was added iron powder (325 mesh; 4.13 g, 74.0 mmol). To the resulting mixture was added 2,2,7-trifluoro-6-nitro-4-(prop-2-ynyl)-2Hbenzo[b][1,4]oxazin-3(4H)-one (7.06 g, 24.67 mmol) in methanol/tetrahydrofuran. The resulting mixture was stirred vigorously at 70° C. for 2 hours. The reaction was quenched in water/ethyl acetate under stirring. The resulting 2 phase system was filtered and the layers were separated. The water layer was subsequently extracted with ethyl acetate. The combined organic phases were washed with brine, dried with Na$_2$SO$_4$ and concentrated to yield 5.15 g of the title compound.

GCMS m/e (M+)=256

1.7: 2,2,7-trifluoro-6-isocyanato-4-(prop-2-ynyl)-2Hbenzo[b][1,4]oxazin-3(4H)-one

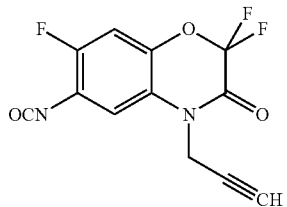

To 6-amino-2,2,7-trifluoro-4-(prop-2-ynyl)-2H-benzo[b][1,4]oxazin-3(4H)-one (5.1 g, 19.91 mmol) in dry toluene was dropwise added diphosgene (2.64 ml, 21.90 mmol) in dry toluene. The resulting mixture was stirred overnight at reflux. The mixture was concentrated and chased with toluene and used as such in the next step.

1.8: 6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione

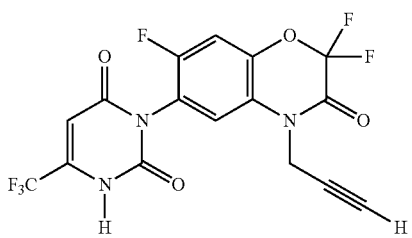 [SMILES: C#CCN1C(=O)C(F)(F)Oc2cc(F)c(-n3c(=O)cc(C(F)(F)F)[nH]c3=O)cc21]

A solution of (E)-ethyl 3-amino-4,4,4-trifluorobut-2-enoate (4.24 g, 23.2 mmol) was added dropwise at 5° C. under $N_2$ to a stirred solution of sodium hydride (1.01 g of a 55% suspension in mineral oil, 23.2 mmol) in dry DMF. The light yellow suspension was stirred for 1 hour, while allowing the reaction mixture to warm to room temperature. After that period, a solution of 2,2,7-trifluoro-6-isocyanato-4-(prop-2-ynyl)-2Hbenzo[b][1,4]oxazin-3(4H)-one (6.54 g, 23.2 mmol) in toluene was added dropwise, after which the mixture was heated at 80° C. overnight under nitrogen. As LC/MS indicated that the reaction was not fully complete, heating was continued for a further 3 hours at 100° C., after which the light brown solution was concentrated in vacuo. The dark residue was partitioned between ethyl acetate and aqueous ammonium chloride solution, and the aqueous phase was extracted with additional ethyl acetate. The combined organic fractions were washed with brine and dried over $Na_2SO_4$. Filtration and evaporation of the solvent gave 10.68 g crude brown oil. This was purified by column chromatography (EtOAc:heptane, 20-60%) to give three fractions in which the desired product was the major component (present as a mixture of keto and enol tautomers). These three fractions were combined and further purified by column chromatography, eluting with di-isopropyl ether, to give the product (3.0 g) as an offwhite fluffy solid (94% purity according to NMR, with ca. 20% existing as the enol tautomer).

$^1$H-NMR of the major (keto) tautomer (DMSO): 2.50 (s, 1H), 4.78 (s, 2H), 6.47 (s, 1H), 7.72 (m, 2H), 12.86 (br, 1H). The broad peak at 12.86 ppm disappeared upon H/D exchange (with $D_2O$).

Alternative procedure for the preparation of the final intermediate, 6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, via the carbamate:

1.7a: Ethyl (2,2,7-trifluoro-3-oxo-4-prop-2-ynyl-3,4-dihydro-2H-benzo[1,4]oxazin-6-yl)-carbamate

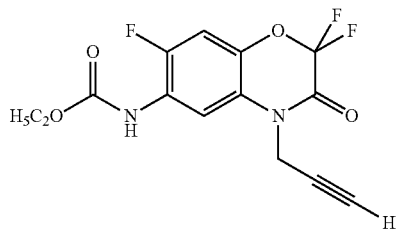

A mixture of 6-amino-2,2,7-trifluoro-4-(prop-2-ynyl)-2Hbenzo[b][1,4]oxazin-3(4H)-one (2.0 g, 7.8 mmol) and ethyl chloroformate (1.14 g, 10.5 mmol) in dry toluene was heated to reflux for 2 hours. The mixture was evaporated to dryness to obtain a brown solid. Column chromatography (silica, EtOAc: heptane, 1:3) gave the product (1.04 g), which was used without further purification in the next step 1.8a.

1.8a: 6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione

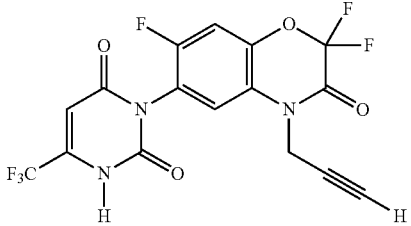 [SMILES: C#CCN1C(=O)C(F)(F)Oc2cc(F)c(-n3c(=O)cc(C(F)(F)F)[nH]c3=O)cc21]

Sodium hydride (24.4 mg, 0.61 mmol) was added to a stirred solution of ethyl (2,2,7-trifluoro-3-oxo-4-prop-2-ynyl-3,4-dihydro-2H-benzo[1,4]oxazin-6-yl)-carbamate (100 mg, 0.31 mmol) in DMF. The mixture was heated to 120° C. for 18 hours. The formation of the desired product was confirmed by LC/MS analysis (the retention time of 1.932 minutes and the mass spectrum were identical to those of an authentic sample, prepared via the isocyanate.

1.9: 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione

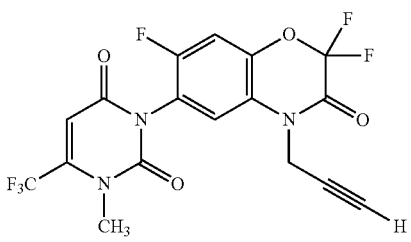 [SMILES: C#CCN1C(=O)C(F)(F)Oc2cc(F)c(-n3c(=O)cc(C(F)(F)F)n(C)c3=O)cc21]

A solution of dimethyl sulfate (0.36 g, 2.86 mmol) in dichloromethane was added to a stirred solution of 6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (1.0 g, 2.4 mmol) and diisopropylethylamine (0.62 g, 4.8 mmol) in dichloromethane at room temperature. The resulting reaction mixture was heated to 50° C. (external temperature). After stirring for 1 hour at this temperature, thin layer chromatography (tlc) analysis indicated complete conversion. The mixture was diluted with dichloromethane and washed with 1N HCl and saturated bicarbonate solution. The organic phase was dried ($Na_2SO_4$) and evaporated to dryness, giving the crude product as a brown oil. Column chromatography (EtOAc:heptane, 10-45%) afforded a white foam. This was further purified by preparative liquid chromatography to give two fractions:

Fraction 1 (229 mg, purity 93%), and Fraction 2 (264 mg, purity 90%).

$^1$H-NMR of Fraction 1 (DMSO): 2.36 (s, 1H), 3.57 (s, 3H), 4.74 (s, 2H), 6.39 (s, 1H), 7.1-7.2 (m, 2H).

Use Examples

The herbicidal activity of the uracils of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has, been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer Code | Scientific name | Common name |
|---|---|---|
| ABUTH | *Abutilon theophrasti* | velvetleaf |
| AMARE | *Amaranthus retroflexus* | common amaranth |
| BRADE | *Brachiaria deflexa* | — |
| BRAPL | *Brachiaria plantaginea* | alexandergrass |
| CHEAL | *Chenopodium album* | lambsquarters |
| COMBE | *Commenline benghalensis* | bengal commenlina |
| DIGSA | *Digitaria sanguinales* | large crabcrass |
| ELFIN | *Eleusine indica* | wiregrass |
| ERICA | *Erigeron canadensis* | Canada horseweed |
| PHBPU | *Pharbitis purpurea* | common morning glory |
| SETFA | *Setaria faberi* | giant foxtail |
| SETVI | *Setaria viridis* | green foxtail |
| SOLNI | *Solanum nigrum* | black nightshade |

At an application rate of 6.25 g/ha, the compound Ia48 applied by the post-emergence method, showed very good herbicidal activity against *Abutilon theophrasti, Amaranthus retroflexus, Chenopodium album* and *Pharbitis purpurea*.

At an application rate of 625 g/ha, the compound Ia48 applied by the pre-emergence method, showed very good herbicidal activity against *Amaranthus retroflexus, Erigeron Canadensis* and *Solanum nigrum*.

TABLE 2

Synergistic herbicidal action of the mixture 1.54 applied by the post-emergence method

| application rate a.s. in g/ha | | herbicidal activity against | | | |
|---|---|---|---|---|---|
| | | BRAPL | | COMBE | |
| Ia48 | B.54 | found | calculated | found | calculated |
| 6.25 | — | 60 | — | — | — |
| 3.12 | — | — | — | 60 | — |
| — | 250 | 20 | — | 70 | — |
| 6.25 | 250 | 85 | 68 | — | — |
| 3.12 | 250 | — | — | 95 | 88 |

TABLE 3

Synergistic herbicidal action of the mixture 1.93 applied by the post-emergence method

| application rate a.s. in g/ha | | herbicidal activity against BRADE | |
|---|---|---|---|
| Ia48 | B.93 | found | calculated |
| 6.25 | — | 85 | — |
| — | 3.1 | 65 | — |
| 6.25 | 3.1 | 95 | 95 |

TABLE 4

Synergistic herbicidal action of the mixture 1.98 applied by the post-emergence method

| application rate a.s. in g/ha | | herbicidal activity against ELEIN | |
|---|---|---|---|
| Ia48 | B.98 | found | calculated |
| 3.12 | — | 20 | — |
| — | 135 | 60 | — |
| 6.25 | 135 | 75 | 68 |

TABLE 5

Synergistic herbicidal action of the mixture 1.118 applied by the post-emergence method

| application rate a.s. in g/ha | | herbicidal activity against DIGSA | |
|---|---|---|---|
| Ia48 | B.118 | found | calculated |
| 6.25 | — | 65 | — |
| — | 12.5 | 35 | — |
| 6.25 | 12.5 | 85 | 77 |

TABLE 6

Synergistic herbicidal action of the mixture 26.98 applied by the post-emergence method

| application rate a.s. in g/ha | | | herbicidal activity against | | | |
|---|---|---|---|---|---|---|
| | | | SETVI | | ERICA | |
| Ia48 | B.76 | B.98 | found | calculated | found | calculated |
| 12.5 | — | — | 95 | — | 90 | — |
| — | 1.56 | — | 0 | — | 45 | — |
| — | — | 68 | 90 | — | 80 | — |
| 12.5 | 1.56 | 68 | 100 | 100 | 100 | 99 |

TABLE 7

Comparison of the herbicidal activity of example 1 of the present invention and example 39 known from WO 90/15057 at an application rate of 0.025 kg/ha pre-emergence eight days after treatment (greenhouse)

| compound | example 1 of the present invention | example 39 known from WO 90/15057 |
|---|---|---|
| application rate [kg/ha] | 0.025 | 0.025 |
| unwanted plants | damages | |
| *Pharbitis purpurea* | 90 | 80 |
| *Setaria faberi* | 98 | 90 |

The test data clearly indicate that the introduction of halogen atoms in 2-positions of the benzo[1,4]oxazine ring results in a superior herbicidal activity as achieved by example 39 known from WO 90/15057, wherein the benzo[1,4]oxazine ring is unsubstituted in the 2-position.

The invention claimed is:

1. A compound of formula V

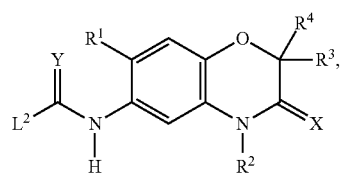

wherein $R^1$ is hydrogen or halogen;

$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$R^3$ is hydrogen or halogen;

$R^4$ is halogen;

X is O or S;

Y is O or S; and $L^2$ is $C_1$-$C_6$-alkoxy, $C_1$-$C_6$-alkylthio or aryloxy, wherein the aryl moiety may itself be partly or fully halogenated and/or may be substituted by from one to three radicals from the group of cyano, nitro, $C_1$-$C_4$-alkyl, $C_1$-$C_4$-alkoxy and $C_1$-$C_4$-alkylthio.

2. The compound V of claim 1, wherein $L^2$ is $C_1$-$C_6$-alkoxy, $C_1$-$C_6$-alkylthio or phenyloxy, wherein the phenyl moiety may itself be partly or fully halogenated and/or may be substituted by from one to three radicals from the group of cyano, nitro, $C_1$-$C_4$-alkyl, $C_1$-$C_4$-alkoxy and $C_1$-$C_4$alkylthio.

3. The compound V of claim 1, wherein $L^2$ is $C_1$-$C_6$-alkoxy, $C_1$-$C_6$-alkylthio or phenyloxy.

4. The compound V of claim 1, wherein $L^2$ is $C_1$-$C_6$-alkoxy.

5. The compound V of claim 1, wherein $L^2$ is $C_1$-$C_6$-alkylthio.

6. The compound V of claim 1, wherein $L^2$ is phenyloxy.

7. The compound V of claim 1, wherein $R^1$ is halogen.

8. The compound V of claim 1, wherein $R^1$ is fluorine.

9. The compound V of claim 1, wherein $R^2$ is $C_3$-$C_6$-alkynyl or $C_3$-$C_6$-haloalkynyl.

10. The compound V of claim 1, wherein $R^2$ is $CH_2C{\equiv}CH$, $CH_2C{\equiv}CCl$ or $CH_2C{\equiv}CBr$.

11. The compound V of claim 1, wherein $R^2$ is $C_3$-$C_6$-alkynyl.

12. The compound V of claim 1, wherein $R^2$ is propargyl.

13. The compound V of claim 1, wherein $R^3$ is halogen.

14. The compound V of claim 1, wherein $R^3$ is fluorine.

15. The compound V of claim 1, wherein $R^4$ is fluorine.

16. The compound V of claim 1, wherein X is oxygen.

17. The compound V of claim 1, wherein Y is oxygen.

18. The compound V of claim 1, wherein Y is sulphur.

* * * * *